(12) United States Patent
Griffey et al.

(10) Patent No.: US 6,730,485 B2
(45) Date of Patent: May 4, 2004

(54) METHODS FOR IDENTIFYING LIGAND BINDING SITES IN A BIOMOLECULE

(75) Inventors: Richard H. Griffey, Vista, CA (US); Steven A. Hofstadler, Oceanside, CA (US); Eric E. Swayze, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 10/210,684

(22) Filed: Jul. 31, 2002

(65) Prior Publication Data

US 2003/0013113 A1 Jan. 16, 2003

Related U.S. Application Data

(62) Division of application No. 09/791,147, filed on Feb. 22, 2001, now Pat. No. 6,653,067.

(51) Int. Cl.⁷ .......................... C12Q 1/68; C07H 19/00; C07H 21/00; C07H 21/02
(52) U.S. Cl. ................. 435/6; 435/5; 435/7.1; 435/7.2; 536/22.1; 536/23.1
(58) Field of Search ........................ 435/5, 6, 7.1, 7.2; 536/22.1, 23.1

(56) References Cited

U.S. PATENT DOCUMENTS

| 6,060,248 A | 5/2000 | Lane et al. ............... 435/6 |
| 6,329,146 B1 | 12/2001 | Crooke et al. ............ 435/6 |

FOREIGN PATENT DOCUMENTS

WO    WO 99/45150    11/1999

OTHER PUBLICATIONS

Amster, I. J., "Fourier Transform Mass Spectrometry," *Jour. Of Mass Spectrometry*, 1996, 31, 1325–1337.

Anderegg, R. J. et al., "Mass Spectrometric Characterization of a Protein–Ligand Interaction," *J. Am. Chem. Soc.*, 1995, 117, 1374–1377.

Ayed, et al., "*Quantitative Evaluation of Protein–Protein and Ligand–Protein Equilibria of a Large Allosteric Enzyme by Electrospray Ionization Time–of–flight Mass Spectrometry*", *Rapid Commun. Mass Spectrom.*, 1998, 12, 339–344.

Baca, M. et al., "Direct Observation of a Ternary Complex between the Dimeric Enzyme HIV–1 Protease and a Substrate–Based Inhibitor," *J. Am. Chem. Soc.*, 1992, 114, 3992–3993.

Bachelin et al., "Structure of a stereoregular phosphorothioate DNA/RNA duplex," *Nat. Struct. Biol.*, 1998, 5(4), 271–276.

Baczynskyj et al., "Application of Thermally Assisted Electrospray Ionization Mass Spectrometry for Detection of Noncovalent Complexes of Bovine Serum Albumin with Growth Hormone Releasing Factor and Other Biologically Active Peptides", *Rapid Commun. Mass Spectrom.*, 1994, 8, 280–286.

Bayer, E. et al., "Analysis of Double–Stranded Oligonucleotides by Electrospray Mass Spectrometry", *Anal. Chem.*, 1994, 66, 3858–3863.

(List continued on next page.)

Primary Examiner—Jezia Riley
(74) Attorney, Agent, or Firm—Christine A. Goddard; Paul K. Leggard; Kenneth H. Tarbet

(57) ABSTRACT

Methods of identifying ligand binding sites in a target molecule such as a polynucleotide or polypeptide, as well as methods for determining whether a particular site in a target molecule is at or near the ligand binding site, are provided. Ligand binding affinities corresponding to both the target molecule and a modified version thereof are compared, preferably using mass spectral analysis. The modified molecules, or test molecules, incorporate a modification capable of modulating ligand binding affinity when located at or near the ligand binding sites. Binding site information is derived from the known position of the modification.

19 Claims, 6 Drawing Sheets

OTHER PUBLICATIONS

Berson et al, "General Principles of Radioimmunoassay", *Clin. Chim. Acta,* 1968, 22, 51–60.

Biemann, K., "Mass Spectrometry of Peptides and Proteins," *Ann. Rev. Biochem.,* 1992, 61, 977–1010.

Bowers, M. T. et al., "Mass Spectrometry: Recent Advances and Future Directions," *J. Phys. Chem.,* 1996, 100, 12897–12910.

Bruins, A. P. et al., "Ion Spray Interface for Combined Liquid Chromatography/Atmospheric Pressure Ionization Mass Spectrometry," *Anal. Chem.,* 1987, 59, 2642–2646.

Burlingame, A. L. et al., "Mass Spectrometry," *Anal. Chem.,* 1998, 70, 647R–716R.

Busman, M. et al., "Observation of Large Multimers in the Electrospray Ionization Mass Spectrometry of Peptides," *Rapid Communications in Mass Spectrometry,* 1994, 8, 211–216.

Cai, J. et al., "Capillary electrophoresis–mass spectrometry," *Jour. Of Chromatography,* 1995, 703, 667–692.

Chan et al., "Mapping the Substrate Binding Site of the Prostaglandin Transporter PGT by Cysteine Scanning Mutagenesis", *J. Biol. Chem.,* 1999, 274, 25564–25570.

Chanfreau, et al., "Catalytic Site Components Common to Both Splicing Steps of a Group II Intron", *Science,* 1994, 266, 1383–1387.

Cheng, X. et al., "Using Electrospray Ionization FTICR Mass Spectrometry to Study Competitive Binding of Inhibitors to Carbonic Anhydrase," *J. Am. Chem. Soc.,* 1995, 117, 8859–8860.

Cheng, X. et al., "Direct measurement of oligonucleotide binding stoichiometry of gene V protein by mass spectrometry", *Proc. Natl. Acad. Sci USA,* 1996, 93, 7022–7027.

Cohen, S. L. et al., "Probing the solution structure of the DNA–binding protein Mas by a combination of proteolysis and mass spectrometry," *Protein Science,* 1995, 4, 1088–1099.

Crain et al., "Applications of mass spectrometry to the characterization of oligonucleotides and nucleic acids", *Curr. Opin. Bioetechnol.,* 1998, 9, 25–34.

Cunningham et al., "High–Resolution Epitope Mapping of hGH–Receptor Interactions by Alanine–Scanning Mutagenesis", *Science,* 1989, 244, 1081–1085.

Doctycz et al., "Accumulation and Storage of Ionized Duplex DNA Molecules in a Quadrupole Ion Trap", *Anal. Chem.,* 1994, 66, 3416–3422.

Erikson and Fesik, *Ann. Rep. in Med. Chem.,* 1992, 27, 271–289.

Erlanson, et al., "Site–directed Ligand Discovery", *Proc. Natl. Acad. Sci. USA,* 2000, 97, 9367–9372.

Feng, R. et al., "Analysis of Antibodies and Other Large Glycoproteins in the Mass Range of 150 00–200 000 Da by Electrospray Ionization Mass Spectrometry," *Anal. Chem.,* 1992, 64, 2090–2095.

Fitzgerald, M. et al., "Probing the Oligomeric Structure of an Enzyme by Electrospray Ionization Time–of–flight Mass Spectrometry", *Proc. Natl. Acad. Sci. USA,* 1996, 93, 6851–6856.

Fitzgerald et al., Standing and Chernushevich, Eds., *New Methods for the Study of Biomolecular Complexes, Proceedings of the NATO Advanced Research Workshop, held 16–20 June 1996, in Alberta, Canada, in NATO ASI Ser., Ser. C,* 1998, 510, 1–353, Kluwer, Dordrecht, Netherlands.

Freitas, M. et al., "Determination of Relative Ordering of Activiation Energies for Gas–Phase Ion Unimolecular Dissociation by Infrared Radiation for Gaseous Multiphoton Energy Transfer", *J. Am. Chem. Soc.,* 2000, 122, 7768–7775.

Gale, D. C. et al., "Observation of Duplex DNA–Drug Noncovalent Complexes by Electrospray Ionization Mass Spectrometry," *J. Am. Chem. Soc.,* 1994, 116, 6027–6028.

Ganem, B. "Detecting Noncovalent Complexes of Biological Macromolecules: New Applications of Ion–Spray Mass Spectrometry," *Chemtracts–Organic Chemistry,* Jan./Feb. 1–22, 1993.

Ganem, B. "Detection of Oligonucleotide Duplex Forms by Ion–Spray Mass Spectrometry," *Tetrahedron Letts.,* 1993, 34(9), 1445–1448.

Ganguly et al., "Studies of the Ras–GDP and Ras–GTP Noncovalent Complexes by Electrospray Mass Spectrometry", *Tetrahedron,* 1993, 49(36), 7985–7996.

Gao et al., "Screening Derivatized Peptide Libraries for Tight Binding Inhibitors to Carbonic Anhydrase II by Electrospray Ionization–Mass Spectrometry" *J. Med. Chem.,* 1996, 39, 1949–55.

Gårdsvoll et al. "Mapping Part of the Functional Epitope for Ligand Binding on the Receptor for Urokinase–type Plasminogen Activator by Site–directed Mutagenesis", *J. Biol. Chem.,* 1999, 274, 37995–38003.

Gonzalez, et al., *Biochemistry,* "Structural Study of a DNA–RNA Hybrid Duplex with a Chiral Phosphorothioate Moiety by NMR: Extraction of Distance and Torsion Angle Constraints and Imino Proton Exchange Rates", *Biochemistry,* 1994, 33, 11062–11072.

Goodlett, D. R. et al., "Direct Observation of a DNA Quadruplex by Electrospray Ionization Mass Spectrometry," *Biological Mass Spectrometry,* 1993, 22, 181–183.

Griffey et al., "Detection of base pair mismatches in duplex DNA and RNA oligonucleotides using electrospray mass spectrometry", *Proc. SPIE–Int. Soc. Opt. Eng.,* 1997, 2985, 82–86.

Griffey, et al., "Characterization of Low–Affinity complexes Between Rna and Small Molucules Using Electrospray Ionization Mass Spectrometry", *J. Am. Chem. Soc.,* 2000, 122, 9933–9938.

Griffey, et al., "Determinants of Aminoglycoside–binding Specificity for rRNA by Using Mass Spectrometry", *Proc. Natl. Acad. Sci. USA,* 1999, 96, 10129–10133.

Henion, J. et al., "Mass Spectrometric Investigations of Drug–Receptor Interactions," *Therapeutic Drug Monitoring,* 1993, 15, 563–569.

Hu, P. et al., "Determining Calcium–binding Stoichiometry and Cooperativity of Parvalbumin and Calmodulin by Mass Spectrometry," *Jour. Of Mass Spectrometry,* 1995, 30, 1076–1082.

Huang, E. et al., "Packed–Capillary Liquid Chromatography/Ion–Spray Tandem Mass Spectrometry Determination of Biomolecules," *Anal. Chem.,* 1991, 63, 732–739.

Huang, E. et al., "LC/MS and LC/MS/MS Determination of Protein Tryptic Digests," *Jour. Of the Amer. Soc. Mass Spectrom.,* March/April 1990, 1(2), 158–165.

Jefson, "Applications of NMR of Spectroscopy to Protein Structure Determination," *Ann. Rep. Med. Chem.,* 1988, vol. 23, Ch. 28, 275–283.

Jensen et al., "Mass Spectrometric Characterization of UV–Crosslinked Protein–Nucleic Acid Complexes", *42nd ASMS Conf. On Mass Spectrom. and Allied Topics,* 1994, 923.

Jensen, O. N. et al, "Direct Observation of UV–crosslinked Protein–Nucleic Acid Complexes by Matrix–assisted Laser Desorption Ionization Mass Spectrometry," *Rapid Communications in Mass Spectrometry,* 1993, 7, 496–501.

Jeoung, et al., "Identification of phosphate oxygens that are important for self–cleavage activity of the HDV ribozyme by phosphorothioate substitution interference analysis", *Nucleic Acids Res.,* 1994, 22(18), 3722–3727.

Jönsson, U. et al., "Real–Time Biospecific Interaction Analysis Using Surface Plasmon Resonance and a Sensor Chip Technology," *Biotechniques,* 1991, 11(5), 620–627.

Jorgensen et al., "Direct Determination of Solution Binding Constants for Noncovalent Complexes between Bacterial Cell Wall Peptide Analogues and Vancomycin Group Antibiotics by Electrospray Ionization Mass Spectrometry", *Anal. Chem.,* 1998, 70, 4427–4432.

Karlsson, R. et al., "Kinetic analysis of monoclonal antibody–antigen interactions with a new biosensor based analytical system," *Jour. Of Immunological Methods,* 1991, 145, 229–240.

Kufel, et al., "The P15–loop of *Escherichia coli* RNase P RNA is an autonomous divalent metal ion binding domain", 1998, 4, 777–787.

Lane, T. F. et al., "SPARC Is a Source of Copper–binding Peptides that Stimulate Angiogenesis," *Jour. Of Cell Biology,* May 1994, 125(4), 929–943.

Li, Y. T. et al., "Mass Spectrometric Studies on Noncovalent Dimers of Leucine Zipper Peptides," *J. Am. Chem. Soc.,* 1993, 115, 8409–8413.

Light–Wahl, K. J. et al., "Observation of the Noncovalent Quaternary Associations of Proteins by Electrospray Ionization Mass Spectrometry," *J. Am. Chem. Soc.,* 1994, 116, 5271–5278.

Light–Wahl, K. J. et al., "Observation of a Small Oligonucleotide Duplex by Electrospray Ionization Mass Spectrometry," *J. Am. Chem. Soc.,* 1993, 115, 803–804.

Lim, H. et al., "Recognition of Cell–wall Peptide Ligands by Vancomycin Group Antibiotics: Studies Using Ion Spray Mass Spectrometry," *Jour. Of Mass Spectrometry,* 1995, 30, 708–714.

Little et al, "Verification of 50–to 100–mer DNA and RNA Sequences with High–resolution Mass Spectrometry", *Proc. Natl. Acad. Sci. USA,* 1995, 92, 2318–2322.

Loo, et al., "A Study of Src SH2 Domain Protein—Phosphopeptide Binding Interactions by Electrospray Ionization Mass Spectrometry", *J. Am. Soc. Mass Spectrom.,* 1997, 8, 234–243.

Loo, J. A., "Bioanalytical Mass Spectrometry: Many Flavors to Choose," *Bioconjugate Chem.,* 1995, 6, 644–665.

Loo, J. A. et al., "Use of Electrospray Ionization Mass Spectrometry to Probe Antisense Peptide Interactions," *Biological Mass Spectrometry,* 1994, 23, 6–12.

Loo, J. A., "Observation of Large Subunit Protein Complexes by Electrospray Ionization Mass Spectrometry," *Jour. Of Mass Spectrometry,* 1995, 30, 180–183.

Loo, "Studying Noncovalent Protein Complexes by Electrospray Ionization Mass Spectrometry", *Mass Spectrometry Reviews,* 1997, 16, 1–23.

Loo, J. A. et al., "Interaction of Angiotensin Peptides and Zinc Metal Ions Probed by Electrospray Ionization Mass Spectrometry," *J. Am. Soc. Mass Spectrom.,* November, 1994, 5(11), 959–965.

Marcote et al., "A Three–Dimensional Model of the Cdc2 Protein Kinase: Localization of Cyclin–and Suc1 Binding Regions and Phosphorylation Sites", *Molecular and Cellular Biology,* 1993, 13(8), 5122–5131.

Marshall et al., "Fourier Transform Ion Cyclotron Resonance Mass Spectrometry: A Primer", *Mass Spectrom. Rev.,* 1998, 17, 1–35.

Marshall, A. G. et al., "Fourier Transform Ion Cyclotron Resonance Mass Spectrometry: The Teenage Years," *Anal. Chem.,* Feb. 15, 1991, 63(4), 215A–229A.

Michels, et al., "Conversion of a Group II Intron into a New Multiple–Turnover Ribozyme That Selectively Cleaves Oligonucleotides: Elucidation of Reaction Mechanism and Structure/Function Relationships" *Biochemistry,* 1995, 34, 2965–2977.

Milligan et al., "Determination of RNA–Protein Contacts Using Thiophosphate Substitutions", *Biochemistry,* 1989, 28, 2849–2855.

Mynarcik et al., "Identification of Common Ligand Binding Determinants of the Insulin and Insulin–Like Growth Factor 1 Receptors", *J. Biol. Chem.,* 1997, 272, 18650–18655.

Nelson, R. W. et al., "Mass Determination of Human Immunoglobulin IgM Using Matrix–assisted Laser Desorption/Ionization Time–of–flight Mass Spectrometry," *Rapid Communications in Mass Spectrometry,* 1994, 8, 627–631.

Ruffner, et al., "Thiophosphate interference experiments locate phosphates important for the hammerhead RNA self–cleavage reaction" *Nucleic Acids, Res.,* 1990, 18, 6025–6029.

Sannes–Lowery, et al., "Measuring Dissociation Constants of RNA and Aminoglycoside Antibiotics by Electrospray Ionization Mass Spectrometry", *Anal. Biochem.,* 2000, 280, 264–271.

Schnier, et al., "Blackbody Infrared Radiative Dissociation of Bradykinin and Its Analogues: Energetics, Dynamics, and Evidence for Salt–Bridge Structures in the Gas Phase", *J. Am. Chem. Soc.,* 1996, 118, 7178–7189.

Schnitzer, et al., Identification of Specific Rp–phosphate Oxygens in the tRNA Anticodon Loop Required for Ribosomal P–site Binding, *Proc. Natl. Acad. Sci. USA,* 1997, 94, 12823–12828.

Skoog, D. A. et al., "The Mass Spectrometer," in *Principles of Instrumental Analysis,* Second Edition, Saunders College, Philadelphia, Pa., 1980, 477–499.

Smith, R. D. et al., "The Observation of Non–covalent Interactions in Solution by Electrospray Ionization Mass Spectrometry: Promise, Pitfalls and Prognosis," *Biological Mass Spectrometry,* 1993, 22, 493–501.

Smith et al., "New Mass Spectrometric Methods for the Study of Noncovalent Associations of Biopolymers", *Chem. Soc. Rev.,* 1997, 26, 191–202.

Smith, et al., "Phosphorothioate Substitution Can Substantially Alter RNA Conformation", *Biochemistry,* 2000, 39, 5642–5652.

Smith, R. D. et al., "New Developments in Biochemical Mass Spectrometry: Electrospray Ionization," *Anal Chem.*, 1990, 62, 882–899.

Udenfriend, S. et al., "Scintillation Proximity Assay: A Sensitive and Continuous Isotopic Method for Monitoring Ligand/Receptor and Antigen/Antibody Interactions," *Anal. Biochem.*, 1987, 161, 494–500.

Winger, B. E. et al., "High–Resolution Accurate Mass Measurements of Biomolecules Using a New Electrospray Ionization Ion Cyclotron Resonance Mass Spectrometer," *J. Am. Soc. Mass Spectrom.*, July 1993, 4(7), 566–577.

Witkowska, H. E. et al., "Mass Spectrometric Analysis of a Native Zinc–Finger Structure: The Glucocorticoid Receptor DNA Binding Domain," *J. Am. Chem. Soc.*, Mar. 12, 1995, 117(12), 3319–3324.

Yan et al., "Structural Features of the Ligand–binding Domain of the Serotonin $5HT_3$ Receptor", *J. Biol. Chem.*, 1999, 274, 5537–5541.

Chen, Q., et al., "Structure–Based Discovery of Ligands Targeted to the RNA Double Helix," Biochemistry (1997) 36: 11402–11407.

| Complex | Fraction Bound | % Control |
|---|---|---|
| 16S+Gentamicin | .127 | |
| 16S(G1491_PS)+Gentamicin | .140 | 110 |
| 16S+Ribostamycin | .105 | |
| 16S(G1491_PS)+Ribostamycin | .100 | 94 |
| 16S+Gentamicin | .121 | |
| 16S(A1492_PS)+Gentamicin | .118 | 97 |
| 16S+Ribostamycin | .101 | |
| 16S(A1492_PS)+Ribostamycin | .082 | 80 |

Gentamicin lacks 'A' ring 3'-OH proximate to A1492[PS]

FIG. 5

METHODS FOR IDENTIFYING LIGAND BINDING SITES IN A BIOMOLECULE

CROSS-REFERENCE TO RELATED APPLICATIONS

This application is a divisional of U.S. Ser. No. 09/791,147 filed Feb. 22, 2001, now U.S. Pat. No. 6,653,067, which is incorporated herein by reference in its entirety.

FIELD OF THE INVENTION

The present invention is directed in general to the areas of detecting and measuring molecular interactions. In particular, the present invention pertains to the identification of ligand binding sites in a biomolecule, preferably using mass spectral analysis.

BACKGROUND OF THE INVENTION

Drug discovery has long been one of the most important areas of pharmaceutical research. New or improved drugs are constantly in demand for the treatment of both established and emerging health threats. Drug discovery has evolved from what was, several decades ago, essentially random screening of natural products, into a scientific process that not only includes the rational and combinatorial design of large numbers of synthetic molecules as potential bioactive agents, such as ligands, agonists, antagonists, and inhibitors, but also includes the identification, mechanistic, and structural characterization of their ligand targets, which may be polypeptides, proteins, or nucleic acids. These key areas of drug design and structural biology are of tremendous importance to the understanding and treatment of disease. However, significant hurdles need to be overcome when trying to identify or develop high affinity ligands for a particular biological target. These include the difficulty surrounding the task of elucidating the structure of targets and targets to which other molecules may be bound or associated, the large numbers of compounds that need to be screened in order to generate new leads or to optimize existing leads, the need to dissect structural similarities and dissimilarities between these large numbers of compounds, correlating structural features to activity and binding affinity, and the fact that small structural changes can lead to large effects on biological activities of compounds.

There are numerous facets to the drug discovery process including not only the identification of potential drug targets, but the determination of the structural and electronic bases of target-drug interactions. Knowledge of target structure has been the basis for rational approaches to drug design, and accordingly a number techniques for the structural elucidation of biologically interesting targets have been developed. For instance, techniques and instrumentation are readily available for the sequencing of proteins and nucleic acids. Presently however, sequencing reveals only primary structure, leaving secondary and tertiary structure to be deduced from theory and physiochemical properties of the molecule. In addition, there are some classes and structures of biopolymeric targets that are not amenable to sequencing efforts.

Another approach to structural elucidation of drug targets and their complexes, resolving some of the deficiencies of sequencing, involves X-ray crystallography. This powerful technique allows for the determination of secondary and tertiary structure of biopolymeric targets and can reveal drug binding sites. As with all techniques, however, it also has limitations. For instance, the data obtained from X-ray crystallography of macromolecules is limited to the quality of crystals being analyzed. Further, crystallization of biopolymers is well known to be extremely challenging, difficult to perform at adequate resolution, and is often considered to be as much an art as a science. Although the wealth of structural information provided by a crystal structure is profound, X-ray crystallography is unable to reveal true insight into the solution-phase, and therefore the biologically relevant, structures of the targets and complexes of interest.

A method that is particularly adept at pinpointing the site of ligand binding in a polypeptide molecule involves systematic site-directed mutagenesis coupled with ligand binding assays. This method is referred to as "alanine scanning" because of the preferred use of alanine variants in the ligand binding assays. Other amino acid substitutions, however, are possible. By systematically replacing each residue in a polypeptide with alanine, a set of mutant proteins can be prepared and assayed by quantitative ligand binding analysis. Changes in ligand binding affinities ($K_D$) for a particular mutation points to certain residues involved in ligand binding. Alanine scanning has been used to map several human biological receptors such as human growth hormone receptor (Cunningham et al., Science, 1989, 244,1081), insulin-like growth factor-1 receptor (Mynarcik et al., J. Biol. Chem., 1997, 272, 18650), seratonin $5HT_3$ receptor (Yan et al., J. Biol. Chem., 1999, 274, 5537), and receptor for urokinase-type plasminogen activator (Gardsvoll et al., J. Biol. Chem., 1999, 274, 37995). Similarly, cysteine scanning has been used to map a transmembrane span within prostaglandin transporter (Chan et al., J. Biol. Chem., 1999, 274, 25564).

Polynucleotides also have been studied using site specific chemical modifications for the study of macromolecular structure and function. For instance, phosphorothioate substitutions in RNA molecules have implicated regions involved in binding metal ions and contacting with other proteins (Ruffner, et al., Nucleic Acids Res., 1990, 18, 6025; Chanfreau, et al., Science, 1994, 266, 1383; Jeoung, et al., Nucleic Acids Res., 1994, 22, 3722; Michels, et al., Biochemistry, 1995, 34, 2965; Kufel, et al., RNA, 1998, 4, 777; Milligan, et al., Biochemistry, 1989, 28, 2849; and Schnitzer, et al., Proc. Natl. Acad. Sci. USA, 1997, 94, 12823). In some cases, phosphorothioate substitutions may cause substantial structural changes in RNA at places remote from the substitution (Smith, et al., Biochemistry, 2000, 39, 5642), but this is most likely peculiar of RNA having complex secondary structure, as the structure of phosphorothioate-modified DNA/RNA duplexes are very similar to that of their unmodified counterparts (Bachelin, et al., Nat. Struct. Biol., 1998, 5,271 and Gonzalez, et al., Biochemistry, 1994, 33, 11062).

Relatively recent progress in the area of mass spectrometry (MS) has allowed this analytical method to play an increasingly important role in drug discovery. Certain advances now allow the detection of large biomolecules and their non-covalent complexes with small molecules. Not only are MS techniques capable of preserving such weak molecular interaction and resolving biomolecules and their complexes, it is fully capable of quantitatively measuring their amounts, allowing for accurate measurement of ligand binding affinities.

Particularly suited for the analysis of biomolecules, electrospray ionization mass spectroscopy (ESI-MS) has been used to study biochemical interactions of biopolymers such as enzymes, proteins and macromolecules such as oligonucleotides and nucleic acids and carbohydrates and their interactions with their ligands, receptors, substrates or inhibitors (Bowers et al., Journal of *Physical Chemistry*, 1996, 100, 12897–12910; Burlingame et al., *J. Anal. Chem.*, 1998, 70, 647R–716R; Biemann, *Ann. Rev. Biochem.*, 1992, 61, 977–1010; and Crain et al., *Curr. Opin. Biotechnol.*, 1998, 9, 25–34). While interactions that lead to covalent modification of biopolymers have been studied for some time, one of the most significant developments in the field has been the observation, under appropriate solution conditions and analyte concentrations, of specific non-covalently associated macromolecular complexes that have been promoted into the gas-phase intact (Loo, *Mass Spectrometry Reviews*, 1997, 16, 1–23; Smith et al., *Chemical Society Reviews*, 1997, 26, 191–202; Ens et al., Standing and Chernushevich, Eds., *New Methods for the Study of Biomolecular Complexes, Proceedings of the NATO Advanced Research Workshop*, held 16–20, Jun. 1996, in Alberta, Canada, in NATO ASI Ser., Ser. C, 1998, 510, Kluwer, Dordrecht, Netherlands).

A variety of non-covalent complexes of biomolecules have been studied using ESI-MS and reported in the literature (Loo, *Bioconjugate Chemistry*, 1995, 6, 644–665; Smith et al., *J. Biol. Mass Spectrom.*, 1993, 22, 493–501; Li et al., *J. Am. Chem. Soc.*, 1993, 115, 8409–8413). These include the peptide-protein complexes (Busman et al., *Rapid Commun. Mass Spectrom.*, 1994, 8, 211–216; Loo et al., *Biol. Mass Spectrom.*, 1994, 23, 6–12; Anderegg and Wagner, *J. Am. Chem. Soc.*, 1995, 117, 1374–1377; Baczynskyj et al., *Rapid Commun. Mass Spectrom.*, 1994, 8, 280–286), interactions of polypeptides and metals (Loo et al., *J. Am. Soc. Mass Spectrom.*, 1994, 5, 959–965; Hu and Loo, *J. Mass Spectrom.*, 1995, 30, 1076–1079; Witkowska et al., *J. Am. Chem. Soc.*, 1995, 117, 3319–3324; Lane et al., *J. Cell Biol.*, 1994, 125, 929–943), and protein-small molecule complexes (Ganem and Henion, *Chem Tracts-Org. Chem.*, 1993, 6, 1–22; Henion et al., *Ther. Drug Monit.*, 1993, 15, 563–569; Ganguly et al., *Tetrahedron*, 1993, 49, 7985–7996, Baca and Kent, *J. Am. Chem. Soc.*, 1992, 114, 3992–3993). Further, the study of the quaternary structure of multimeric proteins (Baca and Kent, *J. Am. Chem. Soc.*, 1992, 114, 3992–3993; Light-Wahl et al., *J. Am. Chem. Soc.*, 1994, 116, 5271–5278; Loo, *J. Mass Spectrom.*, 1995, 30, 180–183, Fitzgerald et al., *Proc. Natl. Acad. Sci. USA*, 1996, 93, 6851–6856), and of nucleic acid complexes (Light-Wahl et al., *J. Am. Chem. Soc.*, 1993, 115, 803–804; Gale et al., *J. Am. Chem. Soc.*, 1994, 116, 6027–6028; Goodlett et al., *Biol. Mass Spectrom.*, 1993, 22, 181–183; Ganem et al., *Tet. Lett.*, 1993, 34, 1445–1448; Doctycz et al., *Anal. Chem.*, 1994, 66, 3416–3422; Bayer et al., *Anal. Chem.*, 1994, 66, 3858–3863; Greig et al., *J. Am. Chem. Soc.*, 1995, 117, 10765–766), protein-DNA complexes (Cheng et al., *Proc. Natl. Acad. Sci. U.S.A.*, 1996, 93, 7022–7027), multimeric DNA complexes (Griffey et al., *Proc. SPIE-Int. Soc. Opt. Eng.*, 1997, 2985, 82–86), and DNA-drug complexes (Gale et al., *JACS*, 1994, 116, 6027–6028) are known in the literature.

ESI-MS has also been effectively used for the determination of binding constants of non-covalent macromolecular complexes such as those between proteins and ligands, enzymes and inhibitors, and proteins and nucleic acids. The use of ESI-MS to determine the dissociation constants ($K_D$) for oligonucleotide-bovine serum albumin (BSA) complexes have been reported (Greig et al., *J. Am. Chem. Soc.*, 1995, 117, 10765–10766). The $K_D$ values determined by ESI-MS were reported to match solution $K_D$ values obtained using capillary electrophoresis.

ESI-MS measurements of enzyme-ligand mixtures under competitive binding conditions in solution afforded gas-phase ion abundances that correlated with measured solution-phase dissociation constants ($K_D$) (Cheng et al., *JACS*, 1995, 117, 8859–8860). The binding affinities of a 256-member library of modified benzenesulfonamide inhibitors to carbonic anhydrase were ranked. The levels of free and bound ligands and substrates were quantified directly from their relative abundances as measured by ESI-MS and these measurements were used to quantitatively determine molecular dissociation constants that agree with solution measurements. The relative ion abundance of non-covalent complexes formed between D- and L-tripeptides and vancomycin group antibiotics were also used to measure solution binding constants (Jorgensen et al., *Anal. Chem.*, 1998, 70, 4427–4432).

ESI techniques have found application for the rapid and straightforward determination of the molecular weight of certain biomolecules (Feng and Konishi, *Anal. Chem.*, 1992, 64, 2090–2095; Nelson et al., *Rapid Commun. Mass Spectrom.*, 1994, 8, 627–631). These techniques have been used to confirm the identity and integrity of certain biomolecules such as peptides, proteins, oligonucleotides, nucleic acids, glycoproteins, oligosaccharides and carbohydrates. Further, these MS techniques have found biochemical applications in the detection and identification of post-translational modifications on proteins. Verification of DNA and RNA sequences that are less than 100 bases in length has also been accomplished using ESI with FTMS to measure the molecular weight of the nucleic acids (Little et al, *Proc. Natl. Acad. Sci. USA*, 1995, 92, 2318–2322).

While data generated and conclusions reached from ESI-MS studies for weak non-covalent interactions generally reflect, to some extent, the nature of the interaction found in the solution-phase, it has been pointed out in the literature that control experiments are necessary to rule out the possibility of ubiquitous non-specific interactions (Smith and Light-Wahl, *Biol. Mass Spectrom.*, 1993, 22, 493–501). The use of ESI-MS has been applied to study multimeric proteins because the gentleness of the electrospray/desorption process allows weakly-bound complexes, held together by hydrogen bonding, hydrophobic and/or ionic interactions, to remain intact upon transfer to the gas phase. The literature shows that not only do ESI-MS data from gas-phase studies reflect the non-covalent interactions found in solution, but that the strength of such interactions may also be determined. The binding constants for the interaction of various peptide inhibitors to src SH2 domain protein, as determined by ESI-MS, were found to be consistent with their measured solution phase binding constants (Loo et al., Proc. $43^{rd}$ ASMS Conf. on Mass Spectrom. and Allied Topics, 1995). ESI-MS has also been used to generate Scatchard plots for measuring the binding constants of vancomycin antibiotics with tripeptide ligands (Lim et al., *J. Mass Spectrom.*, 1995, 30, 708–714).

Similar experiments have been performed to study non-covalent interactions of nucleic acids. ESI-MS has been applied to study the non-covalent interactions of nucleic acids and proteins. Stoichiometry of interaction and the sites of interaction have been ascertained for nucleic acid-protein interactions (Jensen et al., *Rapid Commun. Mass Spectrom.*, 1993, 7, 496–501; Jensen et al., $42^{nd}$ *ASMS Conf on Mass Spectrom. and Allied Topics*, 1994, 923). The sites of interaction are typically determined by proteolysis of either the non-covalent or covalently crosslinked complex (Jensen et al., *Rapid Commun. Mass Spectrom.*, 1993, 7, 496–501; Jensen et al., $42^{nd}$ *ASMS Conf on Mass Spectrom. and Allied Topics*, 1994, 923; Cohen et al., *Protein Sci.*, 1995, 4, 1088–1099). Comparison of the mass spectra with those generated from proteolysis of the protein alone provides information about cleavage site accessibility or protection in the nucleic acid-protein complex and, therefore, information about the portions of these biopolymers that interact in the complex.

Used in conjunction with ESI, Fourier transform ion cyclotron resonance mass spectrometry (FT-ICR MS) is an especially useful analytical technique because of its ability to resolve very small mass differences to make mass measurements with a combination of accuracy and resolution that is superior to other MS detection techniques (Amster, *J. Mass Spectrom.*, 1996, 31, 1325–1337, Marshall et al., *Mass Spectrom. Rev.*, 1998, 17, 1–35). FT-ICR MS, like ion trap and quadrupole mass analyzers, allows selection of an ion that may actually be a weak non-covalent complex of a large biomolecule with another molecule (Marshall and Grosshans, *Anal. Chem.*, 1991, 63, A215-A229; Beu et al., *J. Am. Soc. Mass Spectrom.*, 1993, 4, 566–577; Winger et al., *J. Am. Soc. Mass Spectrom.*, 1993, 4, 566–577; Huang and Henion, *Anal. Chem.*, 1991, 63, 732–739), or hyphenated techniques such as LC-MS (Bruins et al., *Anal. Chem.*, 1987, 59, 2642–2646; Huang and Henion, *J. Am. Soc. Mass Spectrom.*, 1990, 1, 158–65; Huang and Henion, *Anal. Chem.*, 1991, 63, 732–739) and CE-MS experiments (Cai and Henion, *J. Chromatogr.*, 1995, 703, 667–692). FTICR-MS has also been applied to the study of ion-molecule reaction pathways and kinetics.

The use of ESI-FT-ICR mass spectrometry as a method to determine the structure and relative binding constants for a mixture of competitive inhibitors of the enzyme carbonic anhydrase has been reported (Cheng et al., *J. Am. Chem. Soc.*, 1995, 117, 8859–8860). Using a single ESI-FT-ICR MS experiment these researchers were able to ascertain the relative binding constants for the noncovalent interactions between inhibitors and the enzyme by measuring the relative abundances of the ions of these noncovalent complexes. Further, the $K_DS$ so determined for these compounds paralleled their known binding constants in solution. The method was also capable of identifying the structures of tight binding ligands from small mixtures of inhibitors based on the high-resolution capabilities and multistep dissociation mass spectrometry afforded by the FT-ICR technique. A related study (Gao et al., *J. Med. Chem.*, 1996, 39, 1949–55) reports the use of ESI-FT-ICR MS to screen libraries of soluble peptides in a search for tight binding inhibitors of carbonic anhydrase II. Simultaneous identification of the structure of a tight binding peptide inhibitor and determination of its binding constant was performed. The binding affinities determined from mass spectral ion abundance were found to correlate well with those determined in solution experiments. Heretofore, the applicability of this technique to drug discovery efforts is limited by the lack of information generated with regards to sites and mode of such non-covalent interactions between a protein and ligands.

Although there are numerous methods for discovering the particular sites of ligand binding on target molecules, few meet the sensitivity or rapidity with which drug discovery research presently demands. Several methods for determining ligand binding sites have been developed which incorporate the use of mass spectrometry to facilitate analysis of ligand-target interactions. One such method involves the systematic probing of different nucleotide positions in an RNA target molecule in order to find the region that interacts with a ligand of interest. In this method, described in Griffey, et al., *Proc. Natl. Acad. Sci., USA*, 1999, 96, 10129 and in WO 99/45150, ligand binding sites on an RNA molecule are identified by high resolution mass spectrometry from a protection pattern generated by fragmentation of the ligand/RNA complex. More specifically, a single deoxyribose residue, known to be susceptible to infrared multiphoton dissociation cleavage in mass spectrometry experiments, is engineered into the target RNA molecule at a predetermined location. When the deoxyribose residue is located in the vicinity of the ligand binding site, the complexed ligand protects the site from cleavage, rendering a telltale fragmentation pattern detectable by mass spectrometry. This method works best for ligands with relatively high binding affinity since the ligand needs to remain bound to impart a degree of protection to the target while under fragmenting conditions.

Even complex ligand-target systems, where the ligand has multiple weak ligand binding sites, are amenable to analysis by mass spectrometric methods. For instance, an RNA-ligand binary complex was confirmed to be comprised of an ensemble of at least two different complexes, discernable only by the slight differences in ligand binding affinities between the different sites (Griffey, et al., *J. Am. Chem. Soc.*, 2000, 122, 9933).

In other mass spectometric methods, low affinity ligands can be identified by utilizing the formation of a disulfide tether between the ligand and target molecule (Erlanson, et al., *Proc. Natl. Acad. Sci. USA*, 2000, 97, 9367,). The tethered complexes are identified by mass spectrometry, and the position of the tether affords information related to the ligand binding site location. However, this method is limited only to those ligand-target pairs that are capable of forming disulfide linkages. Further, the tethering moiety on the target molecule is required to be located at or near the ligand binding site. Naturally, the limitations imposed by tether formation prevent the general use of this method for determining ligand binding sites.

Therefore, in order to accelerate drug discovery, new and rapid methods for identifying ligand binding sites are needed to provide ways of correlating structural motifs in target molecules with ligand binding affinities, and to design new and more effective drugs having higher binding affinities for their respective targets. Methods along these lines that are applicable to a wide range of drug targets and allow for the systematic probing of biopolymers in conjunction with straightforward and rapid analysis, such as by mass spectrometry, would be of significant value to those presently involved in biochemistry and drug discovery. Indeed, the present invention provides such methods.

SUMMARY OF THE INVENTION

The methods of the present invention generally involve a method for testing whether a predetermined position in a target molecule is at or proximate to a ligand binding site in the target molecule comprising: contacting a ligand with the target molecule under conditions that allow formation of a complex between the target molecule and ligand; contacting the ligand with a test molecule under conditions that allow formation of a complex between the test molecule and ligand, wherein the test molecule is said target molecule comprising a modification at a predetermined position wherein the modification is capable of modulating ligand binding affinity when it is located at or proximate to the ligand binding site of the target molecule; comparing the relative amount of target molecule-ligand complex to the relative amount of test molecule-ligand complex using a mass spectrometer; and determining whether the predetermined position in the target molecule is at or proximate to the ligand binding site, wherein a difference in the relative amounts of target molecule-ligand complex and test molecule-ligand complex indicates that the ligand binds at or proximate to the predetermined position in the target molecule.

In some embodiments, the methods of the present invention include target molecules that can comprise a polynucleotide, oligonucleotide, nucleic acid, peptide nucleic acid, RNA, DNA, RNA/DNA hybrid, peptide, protein, receptor, antibody, oligosaccharide, carbohydrate, or glycoprotein.

In other preferred embodiments, the methods of the present invention include test molecules that may comprise a modified nucleotide or modified amino acid. Modified nucleotides include those having modified nucleobases, modified nucleosidic linking moieties, and modified ribose moieties.

Other embodiments include methods wherein either or both of the target molecule and the test molecule comprise at least one mass tag. Mass tags may be comprised of polymer including polyethylene glycol, polypropylene, polystyrene, cellulose, sephadex, dextran, peptide, polyacrylamide, or the like.

Other embodiments of the present methods include analysis with a mass spectrometer that is capable of producing detectable ions by electrospray ionization, atomospheric pressure ionization, or matrix-assisted laser desorption ionization. The mass spectrometer may also include mass analysis by quadrupole, quadrupole ion trap, time-of-flight, FT-ICR, or hybrid mass detectors.

In yet another embodiment of the present invention, the methods are generally directed to identifying a ligand binding site in a target molecule comprising: contacting a ligand with the target molecule under conditions that allow formation of a complex between the target molecule and ligand; contacting the ligand with a test molecule under conditions that allow formation of a complex between the test molecule and ligand, wherein the test molecule is the target molecule comprising a modification at a predetermined position wherein the modification is capable of modulating ligand binding affinity when it is located at or proximate to the ligand binding site in the target molecule; comparing the relative amount of target molecule-ligand complex to the relative amount of test molecule-ligand complex using a mass spectrometer; determining whether the predetermined position in the target molecule is at or proximate to the ligand binding site, wherein a difference in the relative amounts of target molecule-ligand complex and test molecule-ligand complex indicates that ligand binds at or proximate to the predetermined position in the target molecule; and repeating the contacting, comparing, and determining steps for different predetermined positions in the target molecule until one or more differences are detected, wherein the differences identify the ligand binding site of the target molecule.

In yet another embodiment, the present invention is directed to a method for testing whether a predetermined position in a polynucleotide target molecule is at or proximate to a ligand binding site comprising: contacting a ligand with said polynucleotide target molecule under conditions that allow formation of a complex between said target molecule and said ligand; contacting the ligand with a test molecule under conditions that allow formation of a complex between the test molecule and ligand, wherein the test molecule is target molecule comprising a modification at a predetermined position wherein the modification is capable of modulating ligand binding affinity when it is located at or proximate to the ligand binding site in the target molecule; comparing the ligand binding affinity of the polynucleotide target molecule-ligand complex with the ligand binding affinity of test molecule-ligand complex; and determining whether the predetermined position in said polynucleotide target molecule is at or proximate to the ligand binding site, wherein a difference in the ligand binding affinities of the polynucleotide target molecule-ligand complex and the test molecule-ligand complex indicates that ligand binds at or proximate to the predetermined position in the polynucleotide target molecule.

Other embodiments include a method for identifying a ligand binding site in a polynucleotide target molecule comprising: contacting a ligand with said polynucleotide target molecule under conditions that allow formation of a complex between the target molecule and the ligand; contacting ligand with a test molecule under conditions that allow formation of a complex between the test molecule and ligand, wherein the test molecule is target molecule comprising a modification at a predetermined position wherein the modification is capable of modulating ligand binding affinity when it is located at or proximate to said ligand binding site in the target molecule; comparing the ligand binding affinity of polynucleotide target molecule-ligand complex with the ligand binding affinity of test molecule-ligand complex, determining whether the predetermined position in the polynucleotide target molecule is at or proximate to the ligand binding site, wherein a difference in the ligand binding affinities of the polynucleotide target molecule-ligand complex and the test molecule-ligand complex indicates that ligand binds at or proximate to the predetermined position in the polynucleotide target molecule; and repeating the contacting, comparing, and determining steps for different predetermined positions in the polynucleotide target molecule until one or more differences in ligand binding affinity are detected, wherein the differences identify the ligand binding site of the polynucleotide target molecule.

In yet another embodiment, the present invention is directed to a method of identifying a ligand binding site in a target molecule comprising: contacting a ligand with target molecule under conditions that allow formation of a complex between the target molecule and ligand; contacting ligand with a set of test molecules under conditions that allow formation of complexes between ligand and test molecules, wherein each test molecule of the set is target molecule comprising a modification at a predetermined position, wherein the predetermined position is different for each test molecule of the set, wherein the modification is capable of modulating ligand binding affinity when it is located at or proximate to the ligand binding site of the target molecule, and wherein each test molecule of the set further comprises at least one mass tag substantially differentiating each of the test molecules of the set by mass; comparing the relative amount of target molecule-ligand complex to the relative amount of each test molecule-ligand complex using a mass spectrometer; and determining whether the predetermined position of each of the test molecules of said set is at or proximate to the ligand binding site, wherein a difference in the relative amount of target molecule-ligand complex and the relative amount of each test molecule-ligand complex indicates that ligand binds at or proximate to the predetermined position, wherein one or more differences identify the ligand binding site.

Other embodiments of the present invention provide for a method for testing whether a predetermined position in a target molecule is at or proximate to a binding site for a ligand in a target molecule comprising more than one binding site for the ligand: contacting the ligand with target molecule under conditions that allow formation of a binary complex between ligand and target molecule; contacting ligand with a test molecule under conditions that allow formation of a binary complex between ligand and test molecule, wherein the test molecule is target molecule comprising a modification at a predetermined position wherein the modification is capable of modulating ligand binding affinity when it is located at or proximate to at least one of the ligand binding sites in the target molecule; subjecting the binary ligand complexes to a preselected dissociation energy, causing dissociation of at least some of the binary ligand complexes; comparing the relative amount of remaining undissociated target molecule binary ligand complex with the relative amount of remaining undissociated test molecule binary ligand complex; repeating the previous steps for different preselected dissociation energies, wherein the relationship between dissociation energies and the relative amounts of remaining undissociated target molecule binary ligand complex indicates the dissociation rate of target molecule binary ligand complex, and wherein the relationship between dissociation energies and the relative amounts of remaining undissociated test molecule binary ligand complex indicates dissociation rate of the test molecule binary ligand complex; and comparing the dissociation rate of the target molecule binary ligand complex with the dissociation rate of the test molecule binary ligand complex, wherein a difference in dissociation rates indicates that the predetermined position is at or proximate to one of the ligand binding sites in the target molecule.

In further embodiments, the present invention encompasses a method of identifying a binding site of a ligand in a target molecule comprising more than one binding site for the ligand, comprising: contacting ligand with target molecule under conditions that allow formation of a binary complex between ligand and target molecule; contacting ligand with a test molecule under conditions that allow formation of a binary complex between ligand and test molecule, wherein the test molecule is target molecule comprising a modification at a predetermined position wherein the modification is capable of modulating ligand binding affinity when it is located at or proximate to at least one of the ligand binding sites in the target molecule; subjecting the binary ligand complexes to a preselected dissociation energy, causing dissociation of at least some of the binary ligand complexes; comparing the relative amount of remaining undissociated target molecule binary ligand complex with the relative amount of remaining undissociated test molecule binary ligand complex; repeating the previous steps for different preselected dissociation energies, wherein the relationship between dissociation energies and the relative amounts of remaining undissociated target molecule binary ligand complex indicates dissociation rate of target molecule binary ligand complex, and wherein the relationship between dissociation energies and the relative amounts of remaining undissociated test molecule binary ligand complex indicates dissociation rate of test molecule binary ligand complex; comparing the dissociation rate of target molecule binary ligand complex with dissociation rate of test molecule binary ligand complex, wherein a difference in dissociation rates indicates that the predetermined position is at or proximate to one of the ligand binding sites in the target molecule; repeating the previous steps for different predetermined positions until at least one difference in the dissociation rates is detected; and identifying at least one of the binding sites of ligand in the target molecule, wherein the differences in dissociation rates identify at least one of the ligand binding sites.

BRIEF DESCRIPTION OF THE DRAWINGS

FIG. 5 is a table containing representative data for identification of the gentamicin and ribostamycin binding sites in 16S RNA.

DESCRIPTION OF PREFERRED EMBODIMENTS

Figure 1:
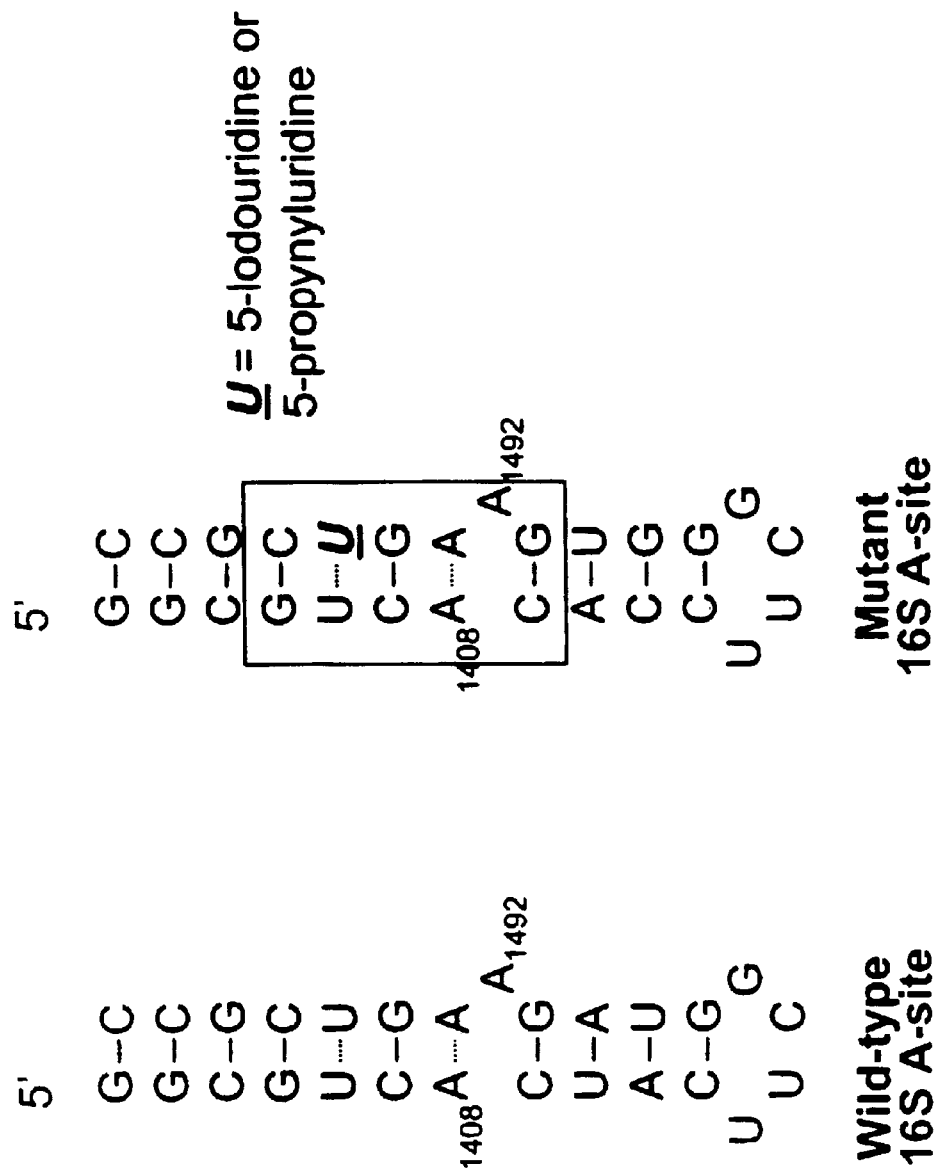
FIG. 1 depicts wild-type (SEQ ID NO:1) and modified (mutant) (SEQ ID NO:2) 27-mer RNA models of the prokaryotic A-site 16S RNA.
Figure 2:
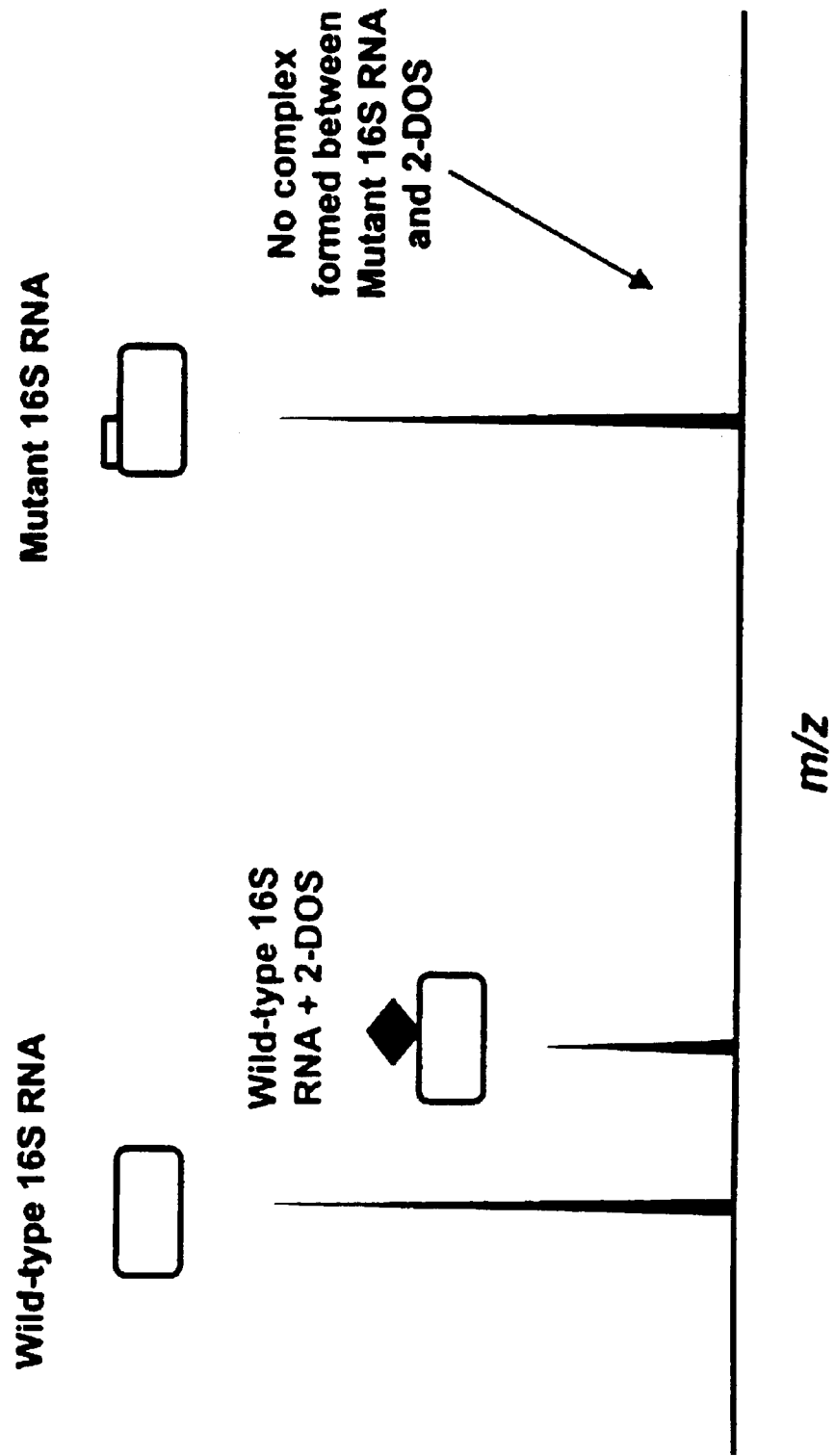
FIG. 2 displays a representative theoretical mass spectra showing 2-deoxystreptamine binding to wild-type and mutant 16S rRNAs generating different ESI-MS signal intensities.

Certain terms are used throughout, and defined hereinbelow, to describe the various preferred embodiments of the present invention. All other terms have their usual meaning as are well known in the art.

The phrases "ligand binding site" or "binding site", used interchangeably, refer to a particular region or regions of a molecule to which a ligand binds to form a non-covalent complex with the molecule. For molecules comprising polynucleotides, the regions may involve one or more individual nucleotides, and for molecules comprising polypeptides, the regions may involve one or more individual amino acid residues.

"Target molecule" or "target," used interchangeably, is meant to refer to a biomolecule containing a ligand binding site. The biomolecule preferably is a biopolymer such as, but not limited to, a polynucleotide or polypeptide.

The term "ligand" is meant to refer to a small molecule having affinity for a target molecule. Generally, the ligand will prefer to bind to the target molecules at one or more particular sites. "Ligand binding affinity" or "binding affinity" refers to the strength of interaction between a target molecule and a ligand. Ligand binding affinity can be measured from the amounts of components of an equilibrium mixture of ligand and target, as is well known in the art, and is expressed as $K_D$, where a large value for $K_D$ represents weak binding affinity and a small value for $K_D$ represents strong binding affinity. Additionally, the site on a biomolecule to which a ligand binds is referred to as a "ligand binding site" and typically includes one or more amino acids or nucleotides within the biomolecule that participate in favorable intermolecular interactions with a ligand The phrase "test molecule," is herein referred to as a molecule substantially identical with a target molecule except for having a modification at a predetermined position. The modification is preferably capable of modulating ligand binding affinity when located at or proximate to the ligand binding site of the target molecule. A test molecule can also differ from a target molecule by comprising a mass tag or other feature which functions to serve as an identifier or marker.

"Predetermined position," as used herein, refers to a region of a target molecule selected for modification in order to determine if that particular region is involved in ligand binding. Selection of the region may be arbitrary or based on prior knowledge of the structure of the target molecule. The region may also be "proximate" to a binding site, the term "proximate" herein referring to being at or in the vicinity of a certain position such as a ligand binding site. Positions "proximate" to a ligand binding site preferably include nucleotides or amino acids less than or about equal to 4 Å from the ligand binding site, and also include any nucleotides or amino acids in van der Waals contact with bound ligand.

As used throughout, the term "modification" refers to an alteration at a predetermined position in the target molecule that preferably allows for the detection of a ligand binding site by modulation of ligand binding affinity when located at or proximate to a ligand binding site. The modification is what substantially distinguishes the target from the test molecule. Modifications generally change structural and/or electronic characteristics of the target molecule at the site the modification is made. Modifications may include sterically bulky moieties of known size (i.e., van der Waal's radii) and contribute to quantification of distances between ligand binding sites and modification sites.

The term "contacting" as used herein, means the bringing together or combining of molecules such that they are within a distance for allowing of intermolecular interactions such as the non-covalent interaction between a target molecule and a ligand. Contacting preferably occurs in solution phase in which the combined or contacted molecules are dissolved in a common solvent and are allowed to freely associate. Contacting is preferably maintained in gas phase. When molecules capable of interacting are contacted or combined under "equilibrium conditions," it is meant to refer to reaction conditions which allow for the combined molecules and their products to reach a steady state such that a constant amount of each reactant and product is present in the mixture. For instance, an equilibrium mixture of target molecule and ligand will comprise steady state amounts of target, ligand, and ligand-target complex, the amounts of which can be used to calculate $K_D$.

"Set of test molecules" or "set," herein used interchangeably, refer to a group of test molecules related to a target molecule. Each of the test molecules of the group are "members" of the set, and each comprise a modification at a unique, predetermined position. That is to say, each member differs from the others primarily by the location of the modification. Members of the set can represent all, or a select number, of the possible modification sites within the target molecule. Members can also comprise mass-modifying tags or "mass tags."

The methods of the present invention are useful for determining positional information with respect to one or more ligand binding sites on a target molecule. Positional information can be obtained by identification of certain groups, moieties, or regions within a target molecule that interact with a ligand. As a non-limiting example, positional information can relate to specific nucleotides or regions of nucleotides in a target molecule comprising a polynucleotide. Further, positional information can relate to specific amino acids or regions of amino acids in a target molecule comprising a polypeptide. Positional information relates to the identification of positions on a target molecule which are either involved and uninvolved in the ligand binding site.

Target molecules include any molecule that is either known or suspected of binding with a ligand. Preferred target molecules include biopolymers, such as polynucleotides and polypeptides, having identifiable repeating units such as nucleotides or amino acids, respectively. Polynucleotides may include oligonucleotides, nucleic acids, peptide nucleic acids, RNA, DNA, or RNA/DNA hybrids. A particularly preferred target molecule is RNA. Polypeptide target molecules include peptides, proteins, receptors, antibodies, or glycoproteins. Other preferred target molecules comprise oligosaccharides, carobohydrates, phospholipids, or glycolipids.

Ligand binding sites include specific regions of the target molecule where a ligand binds to form anon-covalent complex. The ligands themselves are small molecules that form non-covalent complexes with larger target molecules. Preferred ligands are molecules that may potentially modulate activity of the target molecule. For instance, ligands can be agonists or antagonists. In some instances, ligands may be drugs or drug candidates such as antibiotics and the like.

Target molecules can have one or more ligand binding sites. Binding sites for different ligands can share the same region of the target molecule or reside in different locations. Additionally, one ligand can have multiple bindings sites on a target molecule, and each of these binding sites can have different ligand binding affinities. Binding affinity is a measure of the attraction between ligand and target molecule, and is routinely measured by the equilibrium constant of a solution of ligand and target molecule. Strong binding interactions are consistent with high binding affinities which typically range from about 1 nM to about 10 $\mu$M, whereas weak binding interaction have affinities typically ranging from about 10 $\mu$M to about 10 mM.

According to the methods of the present invention, some knowledge of the structure of the target molecule preferably is available in order to obtain positional information of ligand binding sites on a target molecule. Because the present methods involve the probing of regions in the target molecule with regard to their role in modulating ligand binding, primary structure of the regions is preferably known such that positional information related to the ligand binding sites can be systematically determined. As is well known, primary structure relates to the sequence of a molecule. For instance, if the target molecule comprises a polynucleotide or polypeptide, the primary structures would correspond to the sequence of nucleotides or amino acid residues, respectively. Sequencing of polynucleotides and polypeptides are well known in the art and are described in Smith, in *Protein Sequencing Protocols*, Humana Press, Totowa, N.J., 1997; Findlay and Geisow, in *Protein Sequencing: A Practical Approach*, IRL Press, Oxford, 1989; Brown, in DNA Sequencing, IRL Oxford University Press, Oxford, 1994; Adams, Fields and Venter, in *Automated DNA Sequencing and Analysis*, Academic Press, San Diego, 1994, each of which is incorporated herein by reference in its entirety.

Structural information other than primary structure can also be used in determining regions of the target molecule to be probed by the methods of the present invention. Secondary and tertiary structures can aid in determining those regions of the target molecule that would likely or unlikely be involved in ligand binding. In this way, the determination of positional information related to ligand binding sites can be directed to certain regions of a target molecule having secondary or tertiary structural motifs known or suspected of interacting with ligands. Secondary structure of both polynucleotides and polypeptides can be theoretically determined from primary structure. In polypeptides, secondary structure corresponds to motifs such as alpha-helices and beta-sheets, whereas in polynucleotides, secondary structure may correspond to helices, hairpins, bulges, internal loops, junctions, and pseudoknots. Tertiary structure reflects the interactions of secondary structural elements with each other and other regions. Both secondary and tertiary structures can be elucidated by 3-dimensional structure determination methods such as various well known NMR and X-ray crystallographic techniques. Methods for the elucidation of secondary and tertiary structures are provided in Jefson, *Ann. Rep. in Med. Chem.*, 1988, 23, 275; Erikson and Fesik, *Ann. Rep. in Med. Chem.*, 1992, 27, 271–289; Erikson and Fesik, *Ann. Rep. in Med. Chem.*, 1992, 27, 271–289; Copeland, in *Methods of Protein Analysis: A Practical Guide to Laboratory Protocols*, Chapman and Hall, New York, 1994; and Creighton, in *Protein Folding*, W. H. Freeman and Co., 1992, each of which is incorporated herein by reference in its entirety.

The methods of the present invention involve, inter alia, the selection or predetermination of certain positions within the target molecule for their possible involvement in binding ligands. For instance, when the target molecule is a bioplymer, any or all of the repeating units comprising the length of the biopolymer can be selected for testing of a ligand binding site. Repeating units are preferably nucleotides or amino acids, but may be any moiety whose position can be identified in the target molecule. Selection of repeating units for testing can be based on prior knowledge of primary, secondary, or tertiary structures within the target molecule that indicate a probability for ligand binding or non-binding at those sites. For instance, it may be known that a particular ligand binds to an RNA hairpin structure, thus individual nucleotides within the hairpin structure may be selected for testing. On the other hand, if there is no basis for selecting a specific portion of the target molecule for testing, the present methods allow for the systematic testing of each and every repeating unit along the entire length of the target molecule, or those portions of known primary structure, if so desired for determining positional information related to ligand binding.

Once a position along the target molecule has been selected for testing, that position is modified so that it can act as probe of ligand binding affinity at that site. Thus, a modified target molecule, or test molecule, which is the target molecule comprising a modification at a preselected position, is prepared. The modification preferably is capable of affecting ligand binding when proximate to the ligand binding site by either increasing or decreasing ligand binding affinity. Not wanting to be bound by theory, the resulting change in binding affinity is likely due to a perturbation of the non-covalent interactions between the ligand and target molecule arising from differences in steric and/or electronic properties of the test molecule at the binding site. In some embodiments, the modification comprises the introduction of chemical groups that can be characterized as having steric bulk, large van der Waals radii, or different electronic structure relative to those of the target molecule at that position. In this way, the ligand binding site can be sterically and/or electronically altered, thereby affecting the way in which ligand binds.

For certain embodiments where the target molecule comprises a polynucleotide (polynucleotide target molecule), modifications can be made to the individual nucleotides comprising the polynucleotide. In this instance, a specific nucleotide in the target molecule is selected for testing. A modified polynucleotide is then designed that incorporates a modified nucleotide at the selected, or predetermined, nucleotide position. Suitable nucleotide modifications include any modification to a nucleotide believed to be capable of perturbing ligand binding affinity when the modified nucleotide is positioned at or proximate to the ligand binding site. Preferred modified nucleotides include nucleotides having modified nucleobases. Modified nulceobases may include, but are not limited to, 5-substituted pyrimidines such as 5-iodouracil, 5-iodocytosine, and C5-propynyl pyrimidines such as C5-propynylcytosine and C5-propynyluracil. Other suitable modified nucleobases include $N^4$—$(C_1$–$C_{12})$ alkylaminocytosines and $N^4,N^4$—$(C_1$–$C_{12})$ dialkylaminocytosines. Modified nucleobases may also include 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Preferred embodiments of these include, but are not limited to, 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. Furthermore, $N^6$—$(C_1$–$C_{12})$alkylaminopurines and $N^6,N^6$—$(C_1$–$C_{12})$ dialkylaminopurines, including $N^6$-methylaminoadenine and $N^6,N^6$-dimethylaminoadenine, are also suitable modified nucleobases. Similarly, other 6-substituted purines including, for example, 6-thioguanine may constitute appropriate modified nucleobases. Other suitable nucleobases include 2-thiouracil, 8-bromoadenine, 8-bromoguanine, 2-fluoroadenine, and 2-fluoroguanine. Derivatives of any of the aforementioned modified nucleobases are also appropriate for the present invention. Substituents of any of the preceding compounds may include $C_1$–$C_{30}$alkyl, $C_2$–$C_{30}$ alkenyl, $C_2$–$C_{30}$ alkynyl, aryl, aralkyl, heteroaryl, halo, amino, amido, nitro, thio, sulfonyl, carboxyl, alkoxy, alkylcarbonyl, alkoxycarbonyl, and the like. Syntheses of the modified nucleobases, as well as nucleotides and polynucleotides containing the modified nucleobases, are well known to those skilled in the art.

Other preferred modified nucleotides include nucleotides comprising modified nucleosidic linking moieties. Preferred modified nucleosidic linking moieties include, but are not limited to, phosphorothioate, diphosphorothioate, alkylphosphonate, or amidate linking moieties. Syntheses of these and other linking moieties are well known to those skilled in the art.

Other modified nucleotides include nucleotides comprising modification of the 2' position of the ribose moiety. Preferred modified ribose moieties comprise 2' modifications such as 2'-deoxy, 2'-O—$(C_1$–$C_{40})$alkyl, 2'-O-methyl, 2'-O-allyl, 2'-O-dimethylaminoeth 2'-fluoro, 2'-amino, 2'-thio, and 2'-thiomethyl substituents. Method for preparing nucleotides having the above mentioned 2' modifications are well known to those skilled in the art.

For certain preferred embodiments where the target molecule comprises a polypeptide, modifications are made to the individual amino acids. In this instance, a specific amino acid in the target molecule is selected for testing. A modified polypeptide target molecule is then designed that incorporates the modification at the predetermined amino acid position. Suitable amino acid modifications include any change to an amino acid that is believed to be capable of perturbing ligand binding when proximate to the ligand binding site. Preferred amino acid modifications include the substitution of one amino acid for another or the substitution of an amino acid with another moiety. In some preferred embodiments, the modification comprises substitution of an amino acid residue other than alanine with an alanine residue. Syntheses of peptides and polypeptides are well known to those skilled in the art.

The target molecule and the test molecule are combined, or contacted, with a ligand whose binding site is to be determined. Combining, or contacting, preferably occurs in solution, allowing formation of complexes of the ligand with either or both the target molecule and the test molecule. Combining can be performed separately for target molecule and test molecule; however, for ease and convenience, it is preferable that combining be performed using a mixture containing both target and test molecules. The resulting ligand-containing mixtures preferably are at equilibrium, containing equilibrium amounts of unbound target molecule, unbound test molecule, unbound ligand, ligand complexed with target molecule, and ligand complexed with test molecule, depending on the ligand binding affinities. Preferably, target and test molecules are combined with a stoichiometry of 1:1; however, stoichiometries may range from about 10:1 to about 1:10. The stoichiometry for ligand and test or target molecules generally depends on the values for the anticipated dissociation constants and may be readily determined by one skilled in the art. For embodiments employing mass spectrometry for measuring dissociation constants; target molecule, test molecule, and ligand are combined as follows. Preferably, the test and target molecules are purified and dialyzed against a solution of a mass spectrometry-compatible buffer such as 100 mM ammonium acetate. In a typical experiment with a test and target RNA, for example, 100 μL of a 100 μM stock solution of each RNA is prepared following dialysis to remove non-volatile cations such as sodium or potassium. A 1.0 μL aliquot of the test and target RNA is added to 38 1L of a solution containing 100 mM ammonium acetate and 30% v:v isopropyl alcohol. Ligand is added to the desired concentration from a 20 mM stock solution.

The amounts of unbound (free) target molecule, unbound (free) test molecule, ligand complexed with target molecule, and ligand complexed with test molecule present in the equilibrium mixture allow for detection of a differences in binding affinity between the target and test molecules. The difference in relative amounts of target-ligand complex and test-ligand complex upon comparison is reflective of a change in ligand binding affinity resulting from the modification incorporated in the test molecule. Thus, detection of a change in binding affinity indicates that the position of the modification is located at or proximate to the ligand binding site. Conversely, detection of substantially no change in binding affinity indicates that the position of the modification is remote from the ligand binding site.

According to the present invention, changes, or differences, in binding affinity can be measured by any means. Possible methods for measuring binding affinity include analysis by ELISA (Kemeny and Challacombe, in *ELISA and other Solid Phase Immunoassays: Theoretical and Practical Aspects*; Wiley, New York, 1988), radioligand binding assays (Berson and Yalow, *Clin. Chim. Acta*, 1968, 22, 51–60; Chard, in "An Introduction to Radioimmunoassay and Related Techniques," Elsevier press, Amsterdam/New York, 1982), surface-plasmon resonance (Karlsson, Michaelsson and Mattson, *J. Immunol. Methods*, 1991, 145, 229; Jonsson et al., *Biotechniques*, 1991, 11, 620), or scintillation proximity assays (Udenfriend, Gerber and Nelson, *Anal. Biochem.*, 1987, 161, 494–500), each of which are herein incorporated by reference in its entirety. However, in other embodiments, changes in binding affinities are measured by mass spectrometry, for instance, as described in Greig et al., *J. Am. Chem. Soc.*, 1995, 117, 10765–10766; Sannes-Lowery, et al., *Anal. Biochem.*, 2000, 280, 264; Jorgensen, et al., *Anal. Chem.*, 1998, 70, 4427; Ayed, et al., *Rapid Commun. Mass Spectrom.*, 1998, 12, 339; Cheng, et al., *J. Am. Chem. Soc.*, 1995, 117, 8859; Loo, et al., *J. Chem. Soc. Mass Spectrom.*, 1997, 8, 234; and WO 99/45150, each of which is incorporated herein by reference in its entirety.

In general, a change in binding affinity can be determined from the equilibrium mixtures by comparing the relative amounts of ligand complexes for target and test molecules. For instance, a first ratio ($T_L/T$) corresponds to the relative amount, or percentage, of ligand-target complex at equilibrium, where $T_L$ represents the amount of target molecule complexed with ligand (ligand-target complex) and T represents the amount of free target molecule. Similarly, a second ratio ($T^*_L/T^*$) corresponds to the relative amount (such as percentage or mole fraction) of ligand-test complex at equilibrium, where $T^*_L$ represents the amount of test molecule complexed with ligand (ligand-test complex) and $T^*$ represents the amount of free test molecule. Thus, if the first and second ratios are different, the modification at the predetermined position in the test molecule modulates ligand binding affinity, and positional information is directly obtained related to the site of ligand binding in the target molecule. More specifically, one can infer from this result that the site of modification in the test molecule resides at or proximate to the ligand binding site. Conversely, if the first and second ratios are substantially the same (the ratio of second to first ratios is about equal to one), then one can conclude that the modification at the predetermined position in the test molecule does not substantially effect ligand binding, and the predetermined position is unlikely to be involved in ligand binding. When the changes in binding affinity are determined by mass spectrometry, the amounts described above correspond to signal intensities (or ion abundances).

From a more quantitative standpoint, a measure of the affect the modification has on ligand binding can be described by ratio y in Equation 1, shown below. For occasions in which the modification at the predetermined position does not substantially affect ligand binding, y ranges from about 0.95 to about 1.05, or more preferably from about 0.98 to about 1.02, or even more preferably has a value of about 1. For all other values of y, it can be interpreted that the modification at the predetermined position affects ligand binding, thereby providing positional information related to ligand binding site. In this instance, y preferably ranges from about zero to about 0.95. Ratio y may also indicate the way in which the modification affects ligand binding. If y is less than 1, the modification likely lowers ligand binding affinity. This result would be expected for modifications that interfere with ligand binding at the binding site. Conversely, if y is more than 1, the modification likely increases ligand binding affinity.

$$(T^*_L/T^*)/(T_L/T) = y \qquad \text{Equation 1}$$

The identities and amounts of each of the components of the equilibrium mixture (unbound target molecule (T), unbound test molecule ($T^*$), ligand-target complex ($T_L$), and ligand-test complex ($T^*_L$)) can be readily determined by mass spectrometric methods. Mass spectrometry has routinely been used to afford direct and rapid assessment of macromolecules and their interactions with small molecules (ligands). An advantage of mass spectrometry in identifying biological targets and complexes is the sensitivity of the detection process. Ligands which bind to a target through weak noncovalent interactions, can be missed with conventional assays, whereas they are readily detected by mass spectral analysis using the methods and processes of the invention. Not only is mass spectrometry capable of the resolution necessary to detect both a biological target molecule and its complex with a small ligand, it is capable of accurately measuring the relative quantities of each according to ion abundances.

A mass spectrometer analyzes charged molecular ions and fragment ions from sample molecules. These ions and fragment ions are then sorted based on their mass to charge ratio (m/z). A mass spectrum is produced from the abundance of these ions and fragment ions that is characteristic of every compound. In the field of biotechnology, mass spectrometry has been used to determine the structure of a biomolecule, as for instance determining the sequence of oligonucleotides, peptides, and oligosaccharides.

In principle, mass spectrometers consist of at least four parts: (1) an inlet system; (2) an ion source; (3) a mass analyzer; and (4) a mass detector/ion-collection system (Skoog, D. A. and West, D. M., *Principles of Instrumental Analysis*, Saunders College, Philadelphia, Pa., 1980, 477–485). The inlet system permits the sample to be introduced into the ion source. Within the ion source, molecules of the sample are converted into gaseous ions. The most common methods for ionization are electron impact (EI), electrospray ionization (ESI), chemical ionization (CI) and matrix-assisted laser desorption ionization (MALDI). A mass analyzer resolves the ions based on mass-to-charge ratios. Mass analyzers can be based on magnetic means (sector), time-of-flight, quadrupole, quadrupole ion-trap, and Fourier transform mass spectrometry (FTMS). A mass detector collects the ions as they pass through the detector and records the signal. Each ion source can potentially be combined with each type of mass analyzer to generate a wide variety of mass spectrometers.

Mass spectrometry ion sources are well known in the art. Two common ionization methods particularly suitable for large biological targets and their non-covalent complexes are electrospray ionization (ESI) and matrix-assisted laser desorption/ionization (MALDI) (Smith et al., *Anal. Chem.*, 1990, 62, 882–899; Snyder, in Biochemical and Biotechnological Applications of Electrospray Ionization Mass Spectrometry, American Chemical Society, Washington, D.C., 1996; and Cole, in Electrospray Ionization Mass Spectrometry: Fundamentals, Instrumentation, Wiley, New York, 1997). ESI is a preferred method for ionization according to the present invention.

ESI is a gentle ionization method that results in no significant molecular fragmentation and preserves even weakly bound complexes between biopolymers and other molecules so that they are detected intact with mass spectrometry. ESI produces highly charged droplets of the sample being studied by gently nebulizing a solution of the sample in a neutral solvent in the presence of a very strong electrostatic field. This results in the generation of highly charged droplets that shrink due to evaporation of the neutral solvent and ultimately lead to a "coulombic explosion" that affords multiply charged ions of the sample material, typically via proton addition or abstraction, under mild conditions.

Electrospray ionization mass spectrometry (ESI-MS) is particularly useful for very high molecular weight biopolymers such as proteins and nucleic acids greater than 10 kDa in mass, for it affords a distribution of multiply-charged molecules of the sample biopolymer without causing any significant amount of fragmentation. The fact that several peaks are observed from one sample, due to the formation of ions with different charges, contributes to the accuracy of ESI-MS when determining the molecular weight of the biopolymer because each observed peak provides an independent means for calculation of the molecular weight of the sample. Averaging the multiple readings of molecular weight obtained from a single ESI-mass spectrum affords an estimate of molecular weight that is much more precise than would be obtained if a single molecular ion peak were to be provided by the mass spectrometer. Further adding to the flexibility of ESI-MS is the capability of obtaining measurements in either the positive or negative ionization modes.

Fourier transform ion cyclotron resonance mass spectrometry (FT-ICR MS) is an especially useful analytical technique because of its ability to resolve very small mass differences to make mass measurements with a combination of accuracy and resolution that is superior to other MS detection techniques, in connection with ESI ionization (Amster, *J. Mass Spectrom.*, 1996, 31, 1325–1337, Marshall et al., *Mass Spectrom. Rev.*, 1998, 17, 1–35). FT-ICR MS may be used to obtain high resolution mass spectra of ions generated by any of the other ionization techniques. The basis for FT-ICR MS is ion cyclotron motion, which is the result of the interaction of an ion with a unidirectional magnetic field. The mass-to-charge ratio of an ion (m/q or m/z) is determined by a FT-ICR MS instrument by measuring the cyclotron frequency of the ion.

The insensitivity of the cyclotron frequency to the kinetic energy of an ion is one of the fundamental reasons for the very high resolution achievable with FT-ICR MS. Each small molecule with a unique elemental composition carries an intrinsic mass label corresponding to its exact molecular mass, identifying closely related library members bound to a macromolecular target requires only a measurement of exact molecular mass. The target and potential ligands do not require radio labeling, fluorescent tagging, or deconvolution via single compound re-synthesis. Furthermore, adjustment of the concentration of ligand and target allows ESI-MS assays to be run in a parallel format under competitive or non-competitive binding conditions. Signals can be detected from complexes with dissociation constants ranging from less than or equal 1 nM to greater than about 10 mM. FT-ICR MS is an excellent detector in conventional or tandem mass spectrometry, for the analysis of ions generated by a variety of different ionization methods including ESI, or product ions resulting from collisionally activated dissociation.

ESI has found wide acceptance in the field of analytical mass spectrometry since it is a gentle ionization method which produces multiply charged ions from large molecules with little or no fragmentation and promotes them into the gas phase for direct analysis by mass spectrometry. ESI sources operate in a continuous mode with flow rates ranging from <25 nL/min to 1000 $\mu$L/min. The continuous nature of the ion source is well suited for mass spectrometers which employ m/z scanning, such as quadrupole and sector instruments, as their coupling constitutes a continuous ion source feeding in a nearly continuous mass analyzer. As used in this invention the electrospray ionization source may have any of the standard configurations including but not limited to Z-spray, microspray, off-axis spray or pneumatically assisted electrospray. All of these can be used in conjunction with or without additional countercurrent drying gas.

When the solvated ions generated from electrospray ionization conditions are introduced into the mass spectrometer, the ions are subsequently desolvated in an evaporation chamber and may be collected in a rf multi-pole ion reservoir (ion reservoir). A gas pressure around the ion reservoir is reduced to $10^{-3}$–$10^{-6}$ torr by vacuum pumping. The ion reservoir is preferably driven at a frequency that captures the ions of interest and the ensemble of ions are then transported into the mass analyzer by removing or reversing the electric field generated by gate electrodes on either side of the ion reservoir. Mass analysis of the transported or dissociated ions are then performed. Any type of mass analyzers can be used in effecting the methods and process of the invention. These include, but are not limited to, quadrupole, quadrupole ion trap, linear quadrupole, time-of-flight! FT-ICR and hybrid mass analyzers. A preferred mass analyzer is a FT-ICR mass analyzer.

In some embodiments of the present invention, the components of the equilibrium mixture resulting from the contacting of ligand with target and test molecules and containing variable amounts of unbound target molecule, unbound test molecule, ligand complexed with target molecule, and ligand complexed with test molecule, can be measured simultaneously in one MS experiment. However, because the mixture components are resolved according to their mass, those that have the same or similar masses may not be readily distinguishable. For instance, the difference in mass between the target molecule and the test molecule may not be within the capabilities of even the most sensitive of MS instrumentation. Thus, one or more of the target or test molecules may be labeled with mass tags to aid in resolving their respective signals by mass spectrometric methods. In this way, the signals arising from each of the target and test molecules, as well as their respective ligand complexes, are distinct in the mass spectrum resulting in cleanly separated and easily measurable ion peaks.

Mass tags are typically uncharged or positively charged groups such as, but not limited to, alkyl and tetraalkylammonium groups, and polymers such as, but not limited to, polyethylene glycols (PEG), polypropylene, polystyrene, cellulose, sephadex, dextrans, cyclodextrins, peptides, polyacrylamides, and the like. These mass modifying tags may be selected based on their molecular weight contribution and their ionic nature. These mass modifying tags may be attached to the target or test molecules. When the target or test molecules comprise polynucleotides, the mass tag may be attached at one or more sites including, but not limited to, the 2'-O—, 3'-terminus, 5'-terminus or along the sugar-phosphate backbone of nucleic acid targets. Addition of mass modifying tags to the 5'terminus of synthetic oligonucleotides can be realized either using conventional phosphoramidite chemistry, other conventional chemistry or by biochemical or enzymatic means. Such mass modification of a nucleic acid may be carried out using conventional, manual or automated techniques. Alternatively, addition of mass modifying tags may be performed at the 3'-terminus by the use of appropriately modified polymer or CPG supports for solid-phase synthesis of nucleic acids. Mass modification at the 3'terminus may also be done by biochemical or enzymatic means. It is also possible to attach mass modifying tags to the internucleotide linkages of a nucleic acid. This may be performed via the use of appropriately modified phosphoramidites, or other nucleoside building blocks during nucleic acid synthesis or via post-synthetic modification of the internucleotide linkage. Further, attachment of mass modifying tags to nucleic acid targets may also be accomplished via the use of bifunctional linkers at any functional site on the nucleic acid. Similarly, when working with other classes of target and test molecules, these mass modifying tags may likewise be incorporated at one or more positions in the molecule.

In some preferred embodiments of the present invention, mass tags facilitate the simultaneous determination of ligand binding affinities for multiple test molecules. For instance, instead of acquiring individual mass spectra for each test molecule, a plurality of test molecules can be simultaneously screened in one mass spectrum when the test molecules are differentiated with mass tags of different molecular weights. In particular, a set of test molecules may be constructed such that each member possesses a unique modification site, and each modification is correlated with a unique mass tag. In this way, the members of the set may be screened simultaneously for ligand binding affinity because each of the members, and their ligand complexes, can be readily identified by their unique mass. Sets include members representing modifications at all possible sites in the target molecule, or sets include members representing modifications at select sites in the target molecule. Ideally, a set representing modifications at all possible sites in a target molecule can be conveniently analyzed with one mass spectrum, yielding positional information related to one or more ligand binding sites. Although simultaneous screening of all possible members of a set is preferred, it is sometimes more practical to screen a few members of the set at one time, thereby acquiring positional information related to the binding site with more than one mass spectrum. In this case, the number of set members per mass spectrum preferably ranges from about 5 to about 20 test molecules, or more preferably from about 5 to about 10 test molecules, or even more preferably from about 2 to about 5 test molecules.

In many instances, target molecules can have more than one binding site for a particular ligand. The presence of multiple binding sites can result in complex equilibrium mixtures of ligand and target, comprising a number of complexes that cannot be differentiated by mass. For instance, a target molecule having two ligand binding sites can theoretically have two different binary ligand complexes, both of which share the same mass but differ in binding site. Fortunately, different binding sites can be distinguished based on binding affinity, thereby providing a handle with which to determine the presence of a multiple binding site System. As an example, mass spectral methods have been used to demonstrate the ability of a 27-mer RNA model of the 16S rRNA A-site to simultaneously form at least two different 2-deoxystreptamine complexes as disclosed in Griffey, et al, *J. Am. Chem. Soc.*, 2000, 122, 9933, which is incorporated herein by reference in its entirety.

In order to locate the binding site of at least one of the multiple binding sites in the target molecule, a difference in binding affinity between target and test molecules for one of the binding sites can be detected. More particularly, a difference in ligand binding affinity between target and test molecule provides positional information related to at least one of the multiple binding sites. Ligand binding affinity can be correlated with the rate at which ligand dissociates from bound complex. Higher dissociation rates indicate lower binding affinity and, conversely, lower dissociation rates indicate higher binding affinity. Populations of different binary complexes can be differentiated based on dissociation rates because each binding site generally is characterized by a unique binding affinity, however, this information does not yield the position of the binding sites. Thus, by making a modification in the target at a predetermined position and assessing the effect the modification has on dissociation rate, one can determine positional information related to at least one binding site.

Dissociation rates can be measured by any means known to one skilled in the art. Preferably, dissociation rate is determined by subjecting a ligand complex to a range of dissociation energies which effect some degree of dissociation to the complex. The amount of dissociation can be measured by, for example, comparison of the initial amounts of complex with the amounts of remaining complex after dissociation, dissociated ligand, or dissociated target. The amount of dissociation can be correlated with energy, yielding a relationship indicative of ligand binding behavior. In some instances, and for some energy regions, the relationship may be roughly linear, affording simple calculation of dissociation rate which is reflected in the slope of the line (determined, for instance, by linear regression analysis). Different slopes are indicative of different dissociation rates. Methods for determining dissociation rate are described in Schnier, et al., *J. Am. Chem. Soc.*, 1996, 118, 7178 and Freitas, et al., *J. Am. Chem. Soc.*, 2000, 122, 7768, each of which is incorporated herein by reference in its entirety.

For complexes with target molecules having more than one ligand binding site, often, dissociation rates are complex as a result of the variable contributions from the simultaneous formation of several different binary complexes, and do not necessarily follow a single linear or sigmoidal relationship. Instead, the relationship may be comprised of a number of roughly linear regions separated by non-linear regions indicating a change in contribution. For instance, in the low dissociation energy region, the amount of remaining complex may have contributions from more than one binding site. However, in the higher dissociation energy regions, only the strongest binding sites will contribute, the weaker ones having been completely dissociated. Thus, linear regions of the relationship are likely indicative of contributions from a set of binding sites, the non-linear regions indicating changes to the set.

According to the present invention, comparison of dissociation rates between binary ligand complexes of target and test molecules allows for the determination and identification of ligand binding sites. In some embodiments, binary ligand complexes of target and test molecules are subjected to dissociation energies which effect a degree of dissociation of the complex. Dissociation energies are preferably capable of selectively interfering with non-covalent intramolecular interactions. In this way, complexes are dissociated into substantially intact target and test molecules which can be measured. Dissociation energies can be determined or calibrated according to a standard ligand such as ammonium. Preferred dissociation energies range from about the energy needed to completely dissociate bound ammonium ions from the target molecule to about the energy needed to dissociate about 50% of bound ligand from target molecules. Other suitable dissociation energies may range from the energy required to effect from about 10% to about 90% dissociation, or more preferably from about 5% to about 95% dissociation, or even more preferably from about 1% to about 99% dissociation. Sources of dissociation energies include any energy source capable of effecting dissociation, however, preferred sources include infrared or far UV multiphoton irradiation with a pulsed or continuous laser source, blackbody heating, or collisional activation with neutral gases such as He, Ne, Ar, Xe, $N_2$, $CO_2$, or the like.

In preferred embodiments, the binary ligand complexes of target and test molecules are subjected to dissociation energy after having been ionized by a mass spectrometer, such as by electrospray ionization. The ions, containing dissociated products after having been exposed to dissociation energy, are then detected and their ion abundances measured. This procedure is preferably repeated a number times for different dissociation energies representing a range as defined above. Preferably, the number of different dissociation energies tested ranges from about 5 to about 20, or more preferably from about 5 to about 15, or even more preferably from about 5 to about 10. The relative amounts of remaining undissociated binary complexes for both target and test molecules can then be correlated with their respective dissociation energies in order to determine their respective dissociation rates.

Dissociation rates can be compared between test and target complexes, the differences of which are indicative of perturbations in ligand binding affinity of at least one binding site. Changes, or differences, in dissociation rate may be observed for the entire range of dissociation energies or for only a portion thereof. A change in dissociation rate between target and test complexes, representing a likely change in binding affinity for at least one ligand binding site, is preferably at least about 10% change, or more preferably at least about 20% change, or even more preferably at least about 25% change. These detectable differences in dissociation rate between target and test molecule provide evidence that the modification of the test molecule resides at or near the ligand binding site, thereby identifying at least one ligand binding site of the target molecule.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

EXAMPLES

The following examples illustrate preferred embodiments of the present invention using mass spectrometry. Experiments were performed using a 7.0 Tesla Fourier transform ion cyclotron resonance (FT-ICR) mass spectrometer with an electrospray ionization source operating in the negative mode. A −3000 V difference was employed between the spray tip and the inlet capillary to generate the electrospray. Samples were introduced at a flow rate of 1.5 uL/min using a Harvard syringe pump and a 50 uL glass syringe. The desolvation of the electrospray droplets was aided by a flow of countercurrent gas at 1 L/min. Ions were accumulated for 1.0 sec in an intermediate hexapole ion storage region at $1.0 \times 10^{-5}$ mbar. Following transfer to the FT-ICR analysis cell, the image current was measured over a mass range of 500–4000 m/z. Typically, a total of 32 transients containing 512 kbytes were summed prior to Fourier transformation. The m/z values were calibrated on the signal from the $[M-5H^+]^{5-}$ charge state of the free RNA at 1726.509.

Example 1

Binding of Gentamicin to 27-mer 16S RNA Modified at the Tetra Loop

Figure 3:
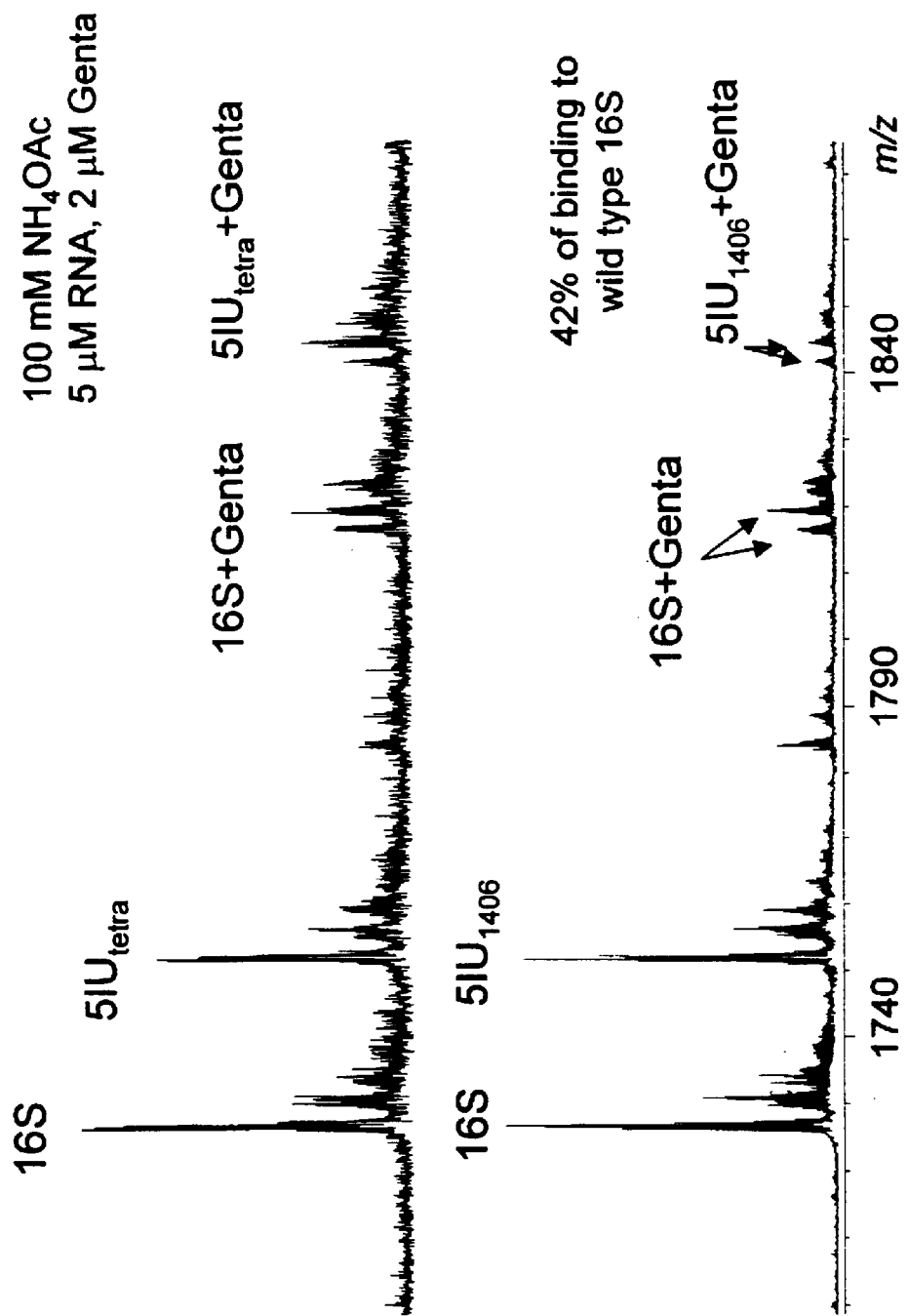
FIG. 3 shows a representative mass spectra results for identification of the gentamicin binding site in 16S RNA.

An aqueous solution containing 100 mM ammonium acetate buffer (pH 7.0), 33% isopropyl alcohol, gentamicin (2 1M, present in three forms), 16S RNA (2.5 $\mu$M) and a modified 16S RNA (2.5 $\mu$M) was prepared. Modified 27-mer 16S RNA contained a 5-iodouridine residue at position 13 in the UUCG tetraloop (See FIG. 1). The resulting mass spectra (see FIG. 3, upper spectrum) contained identifiable peaks corresponding to free 16S RNA (m/z 1726.5), free modified 16S RNA($5IU_{tetra}$; m/z 1750.7), 16S complexed with the three forms of gentamic in present in the sample (16S+genta; m/z 1816–825), and 16S($5IU_{tetra}$) complexed with the three forms of gentamicin ($5IU_{tetra}$+genta; m/z 1841–1849). The peaks were integrated and ion abundances determined. Fractions of 16S+genta and $5IU_{tetra}$+genta complexes were determined to be 70.4% and 68.2±1% for the free 16S RNA and 5IU$_{tetra}$ RNA, respectively. Hence, a 5-iodouridine residue at a site remote from the gentamicin binding site has no effect on the abundance of the gentamicin-RNA complex.

Example 2

Binding of Gentamicin to 27-mer 16S RNA Modified at U$_{1406}$

An aqueous solution containing 100 mM ammonium acetate buffer (pH 7.0), 33% isopropyl alcohol, gentamicin (2 μM), 16S RNA (2.5 μM) and a modified 16S RNA (2.5 μM) was prepared. Modified 27-mer 16S RNA contained a 5-iodouridine residue at position U1406 at the position of a U—U mismatch base pair (E. coli numbering system). The resulting mass spectra (see FIG. 3, lower spectrum) contained identifiable peaks corresponding to free 16S RNA (m/z 1726.5), free modified 16S RNA(5IU$_{1406}$; m/z 1750.7), 16S complexed with the three forms of gentamicin present in the sample (16S+genta; m/z 1816–1825), and 16S (5IU$_{1406}$) complexed with the three forms of gentamicin (5IU$_{1406}$+genta; m/z 1841–1849). The peaks were integrated and ion abundances determined. Fractions of 16S+genta and 5IU$_{1406}$+genta complexes were determined to be 66.8% and 28.1+1% for the free 16S RNA and 5IU$_{1406}$RNA, respectively. The amount of 5IU$_{1406}$+genta was calculated to be 42% of the amount of 16S+genta, indicating that the 5-iodouridine substitution at position 1406 reduces the ability of gentamicin to bind to the RNA, and thus U1406 is located at or proximate to the binding site.

Example 3

Binding of Robostamycin to 27-mer 16S RNA Modified at U$_{1495}$

Figure 4:
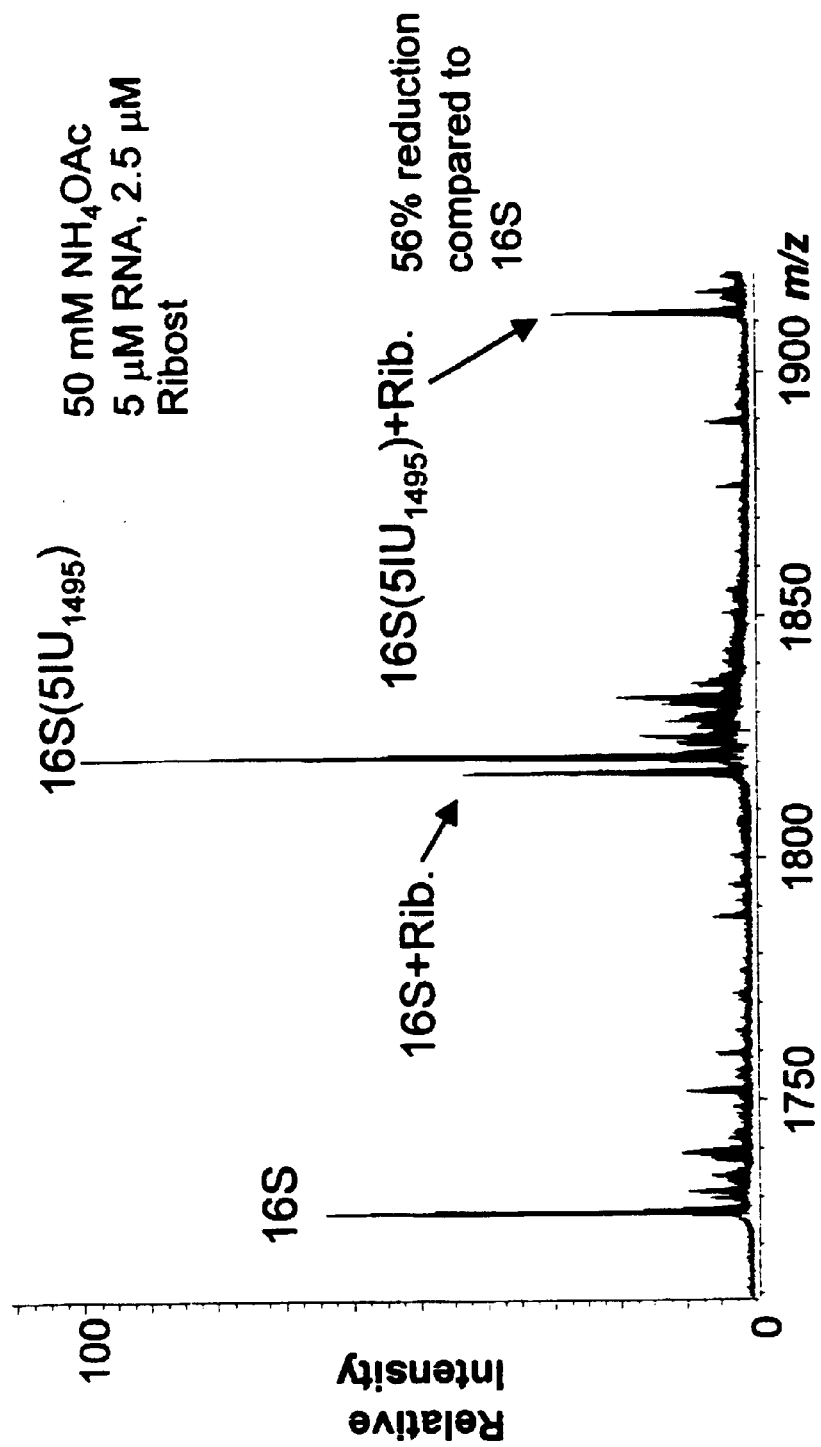
FIG. 4 shows a representative mass spectra results for identification of the ribostamycin binding site in 16S RNA.

An aqueous solution containing 50 mM ammonium acetate buffer (pH 7.0), 33% isopropyl alcohol, ribostamycin (2.5 μM), 16S RNA (2.5 μM) and a modified 16S RNA (2.5 μM) was prepared. Modified 27-mer 16S RNA contained a 5-iodouridine residue at position U1495 at the position of a U—U mismatch base pair (E. coli numbering system) and had a PEG-6 chain synthetically attached to the 5'-hydroxyl group. The resulting mass spectra (see FIG. 4) contained identifiable peaks corresponding to free 16S RNA (m/z 1726.5), free modified 16S RNA(5IU$_{1495}$; m/z 1821.4), 16S complexed with ribostamycin present in the sample (16S+ribost; m/z 1818.6), and 16S(5IU$_{1495}$) complexed with ribostamycin (5IU$_{1495}$+ribost; m/z 1912.3). The peaks were integrated and ion abundances determined. Fractions of 16S+ribost and 5IU$_{1495}$+ribost complexes were determined to be 67.6% and 29.9±1% for the free 16S RNA and 5IU$_{1495}$ RNA, respectively. The amount of 51U$_{1495}$+ribost was calculated to be 44% of the amount of 16S+ribost, indicating that the 5-iodouridine substitution at position 1495 reduces the ability of ribostamycin to bind to the RNA, and thus U1495 is located at or proximate to the binding site on the RNA.

Example 4

Binding of Gentamicin to 27-mer 16S RNA Modified at G$_{1491}$

An aqueous solution containing 100 mM ammonium acetate buffer (pH 7.0), 33% isopropyl alcohol, gentamicin (1 μM), 16S RNA (5 μM) and a modified 16S RNA (5.5 μM) was prepared. Modified 27-mer 16S RNA contained a 3'-phosphorothioate residue at position G1491 at the position of a G-C base pair (E. coli numbering system) and a $C_{12}O_6$ PEG mass tag off the 5'-hydroxyl group. Mass spectra were obtained using the standard protocol described above. The resulting mass spectra contained identifiable peaks corresponding to free 16S RNA (m/z 1726.5), free modified 16S RNA(5'-PS-G1491; m/z 1779.3), 16S complexed with the three forms of gentamicin present in the sample (16S+genta; m/z 1816–1825), and 16S(5'-PS-G1491) complexed with the three forms of gentamicin (5'-PS-G1491+genta; m/z 1869–1875). The peaks from the complexes formed from the lowest mass form of gentamicin were integrated and ion abundances determined. Fractions of 16S+genta and 5'-PS-G1 491+genta complexes were determined to be 0.127 and 0.140±0.01% for the free 16S RNA and 5'-PS-G1491 RNA, respectively. The amount of 5'-PS-G1491+genta was calculated to be 110% of the amount of 16S+genta, indicating that the 5'-PS substitution at position 1491 does not change or slightly enhances the ability of gentamicin to bind to the RNA, and thus G1491 is probably not located at or proximate to the binding site.

Example 5

Binding of Robostamycin to 27 mer 16S RNA Modified at G$_{1491}$

An aqueous solution containing 100 mM ammonium acetate buffer (pH 7.0), 33% isopropyl alcohol, ribostamycin (1 μM), 16S RNA (5 μM) and amodified 16S RNA (5.5 uM) was prepared. Modified 27 mer 16S RNA contained a 3'-phosphorothioate residue at position G1491 at the position of a G-C base pair (E. coli numbering system) and a $C_{12}O_6$ PEG mass tag off the 5'-hydroxyl group. Mass spectra were obtained using the standard protocol described above. The resulting mass spectra contained identifiable peaks corresponding to free 16S RNA (m/z 1726.5), free modified 16S RNA(5'-PS-G1491; m/z 1779.3), 16S complexed with ribostamycin present in the sample (16S+genta; m/z 1818.6), and 16S(5'-PS-G1491) complexed with ribostamycin (5'-PS-GI491+ribost; m/z 1871.4). The peaks from the complexes formed between ribostamycin and the RNA were integrated and ion abundances determined. Fractions of 16S+ribost and 5'-PS-G 1491+ribost complexes were determined to be 0.105 and 0.100±0.005% for the free 16S RNA and 5'-PS-G1491 RNA, respectively. The amount of 5'-PS-G1491+ribost was calculated to be 94% of the amount of 16S+ribost, indicating that the 5'-PS substitution at position 1491 does not interfere with the ability of ribostamycin to bind to the RNA, and thus G1 491 is not located at or proximate to the binding site.

Example 6

Binding of Gentamicin to 27-mer 16S RNA Modified at A$_{1492}$

An aqueous solution containing 100 mM ammonium acetate buffer (pH 7.0), 33% isopropyl alcohol, gentamicin (1 μM), 16S RNA (5 μM) and a modified 16S RNA (5.5 μM) was prepared. Modified 27-mer 16S RNA contained a 3'-phosphorothioate residue at position A1492 at the position of a bulged A residue in the aminoglycoside binding site (E. coli numbering system) and a $C_{12}O_6$ PEG mass tag off the 5'-hydroxyl group. Mass spectra were obtained using the standard protocol described above. The resulting mass spectra contained identifiable peaks corresponding to free 16S RNA (m/z 1726.5), free modified 16S RNA (5'-PS-A1492; m/z 1779.3), 16S complexed with the three forms of gentamicin present in the sample (1 6S+genta; m/z 1816–1825), and 16S(5'-PS-A1492) complexed with the three forms of gentamicin (5'-PS-A1492+genta; m/z 1869–1875). The peaks from the complexes formed from the lowest mass form of gentamicin were integrated and ion abundances determined. Fractions of 16S+genta and 5'-PS-A1492+genta complexes were determined to be 0.121 and 0.118±0.01% for the free 16S RNA and 5'-PS-A1492 RNA, respectively. The amount of 5'-PS-A1492+genta was calculated to be 97% of the amount of 16S+genta, indicating that the 5'-PS substitution at position 1492 does not change or slightly enhances the ability of gentamicin to bind to the RNA, and thus A1492 is probably not located at or proximate to the binding site.

Example 7

Binding of Ribostamycin to 27-mer 16S RNA Modified at $A_{1492}$

An aqueous solution containing 100 mM ammonium acetate buffer (pH 7.0), 33% isopropyl alcohol, ribostamycin (1 μM), 16S RNA (5 μM) and a modified 16S RNA (5.5 1M) was prepared. Modified 27-mer 16S RNA contained a 3'-phosphorothioate residue at position A1492 at the position of a G-C base pair (E. coli numbering system) and a $C_{12}O_6$ PEG mass tag off the 5'-hydroxyl group. Mass spectra were obtained using the standard protocol described above. The resulting mass spectra contained identifiable peaks corresponding to free 16S RNA (m/z 1726.5), free modified 16S RNA(5'-PS-A1492; m/z 1779.3), 16S complexed with ribostamycin present in the sample (16S+genta; m/z 1818.6), and 16S(5'-PS-A1492) complexed with ribostamycin(5'-PS-A1492+ribost; m/z 1871.4). The peaks from the complexes formed between ribostamycin and the RNA were integrated and ion abundances determined. Fractions of 16S+ribost and 5'-PS-A1492+ribost complexes were determined to be 0.101 and 0.082±0.005% for the free 16S RNA and 5'-PS-A1492 RNA, respectively. The amount of 5'-PS-A1492+ribost was calculated to be 80% of the amount of 16S+ribost, indicating that the 5'-PS substitution at position 1492 interferes with the ability of ribostamycin to bind to the RNA, and thus A1492 is located at or proximate to the binding site.

Example 8

Determination of One of at Least Two 2-deoxystreptamine Binding Sites on 27-mer 16S RNA An aqueous solution containing 50 mM ammonium acetate buffer (pH 7.0), 33% isopropyl alcohol, 2-deoxystreptamine (100 μM), 16S RNA (2.5 μM) and a modified 16S RNA (2.5 μM) was prepared. Modified 27mer 16S RNA contained a 5-iodouridine residue at position U1495 at the position of a U—U mismatch base pair (E. coli numbering system) and had a PEG-6 chain synthetically attached to the 5'-hydroxyl group. A series of solution samples (0.75 μL each) were introduced into the mass spectrometer as described above. The voltage difference between the capillary exit and the first skimmer cone was varied between −110 and −180 V in 10 V increments, and a series of spectra were obtained at each value. A similar result could be obtained with infrared multiphoton dissociation using a $CO_2$ laser. The resulting mass spectra contained identifiable peaks corresponding to masses of 16S RNA (16S), modified 16S RNA ($5IU_{1495}$), 16S complexed with 2-DOS (16S+2-DOS), and $5IU_{1495}$ complexed with 2-DOS ($5IU_{1495}$+2-DOS). The peaks were integrated and ion abundances determined for each of the separate runs. Fractions of 16S+2-DOS and $5IU_{1495}$+2-DOS complexes were determined and plotted according to relative energy as depicted in FIG. 6.

Figure 6:
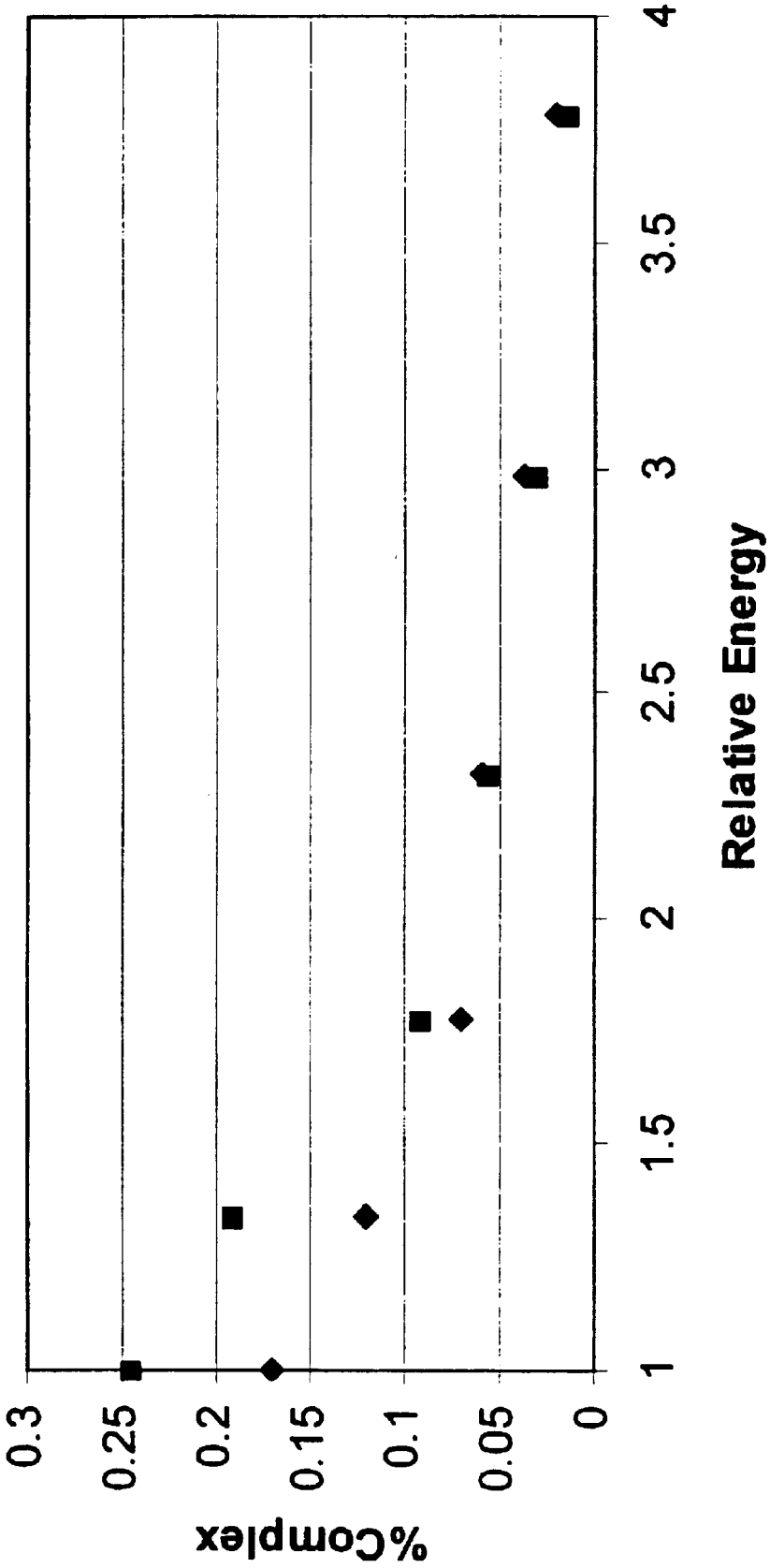
FIG. 6 is a representative graph for identification of one of at least two 2-deoxystreptamine binding sites in 16S RNA.

In FIG. 6, two curves are plotted, corresponding to each of the 16S (diamonds) and $5IU_{1495}$ (squares) systems. Each of the plots show two regions having a substantially linear dissociation rate (slope). The first region of higher slope ranges from 1 to 2 relative energy units, whereas the second region of lower slope ranges from 2 to 4 relative energy units. As is evident from the plot, the slopes in the first region differ significantly (by about 25%) between the 16S and $5IU_{1495}$ systems, indicating that the 5-iodouracil modification at position 1495 modulates binding affinity at a binding site. At energies above about 2 relative energy units, ligand is completely dissociated from the first binding site, leaving contributions from the remaining binding sites. Since, the slopes from the two plots are substantially equal in the higher energy region, the remaining binding site is likely unaffected by the modification at position 1495.

What is claimed is:

1. A method for testing whether a predetermined position in a target molecule is at or proximate to a ligand binding site in said target molecule comprising:
   (a) contacting a ligand with said target molecule under conditions that allow formation of a complex between said target molecule and said ligand;
   (b) contacting said ligand with a test molecule under conditions that allow formation of a complex between said test molecule and said ligand, wherein said test molecule is said target molecule comprising a modification at a predetermined position, wherein said modification is capable of modulating ligand binding affinity when said modification is located at or proximate to said ligand binding site in said target molecule;
   (c) comparing the relative amount of target molecule-ligand complex to the relative amount of test molecule-ligand complex using a mass spectrometer; and
   (d) determining whether said predetermined position in said target molecule is at or proximate to said ligand binding site, wherein a difference in the relative amounts of target molecule-ligand complex and test molecule-ligand complex indicates that said ligand binds at or proximate to said predetermined position in said target molecule.

2. The method of claim 1 wherein said target molecule comprises a polynucleotide, oligonucleotide, nucleic acid, peptide nucleic acid, RNA, DNA, or RNA/DNA hybrid.

3. The method of claim 1 wherein said target molecule comprises a peptide, polypeptide, protein, receptor, or antibody.

4. The method of claim 1 wherein said target molecule comprises an oligosaccharide, carbohydrate, or glycoprotein.

5. The method of claim 1 wherein said test molecule comprises a modified nucleotide.

6. The method of claim 5 wherein said modified nucleotide comprises a modified nucleobase.

7. The method of claim 6 wherein said modified nucleobase comprises 5-substituted pyrimidines, 5-iodouracil, 5-iodocytosine, C5-propynyl pyrimidines, C5-propynylcytosine, C5-propynyluracil, $N^4$—$(C_1-C_{12})$ alkylaminocytosines, $N^4,N^4$—$(C_1-C_{12})$ dialkylaminocytosines, 7-substituted-8-aza-7-deazapurines, 7-substituted-7-deazapurines, 7-iodo-7-deazapurines, 7-cyano-7-deazapurines, 7-aminocarbonyl-7-deazapurines, 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, 2-amino-6-hydroxy-7-aminocarbonyl-7-deazapurines, $N^6$—$(C_1-C_{12})$ alkylaminopurines, $N^6$, $N^6$—$(C_1-C_{12})$dialkylaminopurines, $N^6$-methylaminoadenine, $N^6,N^6$-dimethylaminoadenine, 6-substituted purines, 6-thioguanine, 2-thiouracil, 8-bromoadenine, 8-bromoguanine, 2-fluoroadenine, or 2-fluoroguanine.

8. The method of claim 5 wherein said modified nucleotide comprises a modified nucleosidic linking moiety.

9. The method of claim 8 wherein said modified nucleosidic linking moiety comprises phosphorothioate, diphosphorothioate, alkylphosphonate, or amidate.

10. The method of claim 5 wherein said modified nucleotide comprises a modified ribose moiety.

11. The method of claim 10 wherein said modified ribose moiety comprises 2' modifications selected from the group consisting of 2'-deoxy, 2'-O—$(C_1-C_{40})$alkyl, 2'-O-methyl, 2'-O-allyl, 2'-O-dimethylaminoethyl, 2'-O-methoxyethoxy, 2'-fluoro, 2'-amino, 2'-thio, and 2'-thiomethyl.

12. The method of claim 1 wherein said test molecule comprises a modified amine acid.

13. The method of claim 12 wherein said modified amino acid is alanine.

14. The method of claim 1 wherein either or both of said target molecule and said test molecule comprise at least one mass tag.

15. The method of claim 14 wherein said mass tag comprises polymer.

16. The method of claim 15 wherein said polymer comprises polyethylene glycol, polypropylene, polystyrene, cellulose, sephadex, dextran, peptide, or polyacrylamide.

17. The method of claim 1 wherein said mass spectrometer is capable of producing detectable ions by electrospray ionization, atmospheric pressure ionization, or matrix-assisted laser desorption ionization.

18. The method of claim 1 wherein said mass spectrometer includes mass analysis by quadrupole, quadrupole ion trap, time-of-flight, FT-ICR, or hybrid mass detectors.

19. A method for testing whether a predetermined position in a polynucleotide target molecule is at or proximate to a ligand binding site comprising:
   (a) contacting a ligand with said polynucleotide target molecule under conditions that allow formation of a complex between said target molecule and said ligand;
   (b) contacting said ligand with a test molecule under conditions that allow formation of a complex between said test molecule and said ligand, wherein said test molecule is said target molecule comprising a modification at a predetermined position wherein said modification is capable of modulating ligand binding affinity when said modification is located at or proximate to said ligand binding site in said target molecule;
   (c) comparing the ligand binding affinity of said polynucleotide target molecule-ligand complex with the ligand binding affinity of test molecule-ligand complex; and
   (d) determining whether said predetermined position in said polynucleotide target molecule is at or proximate to said ligand binding site, wherein a difference in the ligand binding affinities of said polynucleotide target molecule-ligand complex and said test molecule-ligand complex indicates that said ligand binds at or proximate to said predetermined position in said polynucleotide target molecule.

* * * * *

UNITED STATES PATENT AND TRADEMARK OFFICE
CERTIFICATE OF CORRECTION

PATENT NO. : 6,730,485 B2
DATED : May 4, 2004
INVENTOR(S) : Richard H. Griffey et al.

It is certified that error appears in the above-identified patent and that said Letters Patent is hereby corrected as shown below:

<u>Column 28,</u>
Line 22, please delete "amine" and insert therefor -- amino --.

Signed and Sealed this

Third Day of May, 2005

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 27
<212> TYPE: RNA
<213> ORGANISM: Artificial Sequence
<220> FEATURE:
<223> OTHER INFORMATION: Novel Sequence

<400> SEQUENCE: 1
ggcgucacua cuucgguaga agucgcc                                          27

<210> SEQ ID NO 2
<211> LENGTH: 27
<212> TYPE: RNA
<213> ORGANISM: Artificial Sequence
<220> FEATURE:
<223> OTHER INFORMATION: Novel Sequence
<220> FEATURE:
<221> NAME/KEY: modified_base
```

```
<222> LOCATION: (23)..(23)
<223> OTHER INFORMATION: 5-iodouracil

<400> SEQUENCE: 2
ggcgucacac cuucggguga agucgcc                                            27
```